(12) United States Patent
Masakari

(10) Patent No.: US 11,781,167 B2
(45) Date of Patent: Oct. 10, 2023

(54) CONTINUOUS GLUCOSE MONITORING USING AN FAD-DEPENDENT GLUCOSE DEHYDROGENASE

(71) Applicant: Kikkoman Corporation, Noda (JP)

(72) Inventor: Yosuke Masakari, Chiba (JP)

(73) Assignee: Kikkoman Corporation, Chiba (JP)

( * ) Notice: Subject to any disclaimer, the term of this patent is extended or adjusted under 35 U.S.C. 154(b) by 31 days.

(21) Appl. No.: 16/318,912

(22) PCT Filed: Mar. 30, 2018

(86) PCT No.: PCT/JP2018/013830
§ 371 (c)(1),
(2) Date: Jan. 18, 2019

(87) PCT Pub. No.: WO2018/181980
PCT Pub. Date: Oct. 4, 2018

(65) Prior Publication Data
US 2019/0185907 A1    Jun. 20, 2019

Related U.S. Application Data

(60) Provisional application No. 62/479,442, filed on Mar. 31, 2017.

(51) Int. Cl.
*C12Q 1/54*    (2006.01)
*C12Q 1/32*    (2006.01)

(52) U.S. Cl.
CPC .............. *C12Q 1/54* (2013.01); *C12Q 1/32* (2013.01); *G01N 2333/90616* (2013.01)

(58) Field of Classification Search
CPC ...... C12Q 1/54; C12Q 1/32; G01N 2333/904; G01N 33/66; G01N 2333/90616; C12Y 101/9901
See application file for complete search history.

(56) References Cited

U.S. PATENT DOCUMENTS

| | | |
|---|---|---|
| 9,260,699 B2 | 2/2016 | Sumida et al. |
| 11,066,690 B2 | 7/2021 | Masakari et al. |
| 2004/0023330 A1 | 2/2004 | Sode |

(Continued)

FOREIGN PATENT DOCUMENTS

| | | |
|---|---|---|
| CN | 102292439 A | 12/2011 |
| EP | 3112461 A1 | 1/2017 |

(Continued)

OTHER PUBLICATIONS

Tchan-Gi Bak, Studies on glucose dehydrogenase of Aspergillus oryzae: II. Purification and physical and chemical properties, 1967, Biochimica et Biophysica Acta (BBA)—Enzymology, vol. 139, Issue 2, pp. 277-293 (Year: 1967).*

(Continued)

*Primary Examiner* — David W Berke-Schlessel
*Assistant Examiner* — Trent R Clarke
(74) *Attorney, Agent, or Firm* — Foley & Lardner LLP

(57) ABSTRACT

Provided is a method of continuous glucose monitoring (CGM) comprising using an FAD-GDH. The FAD-GDH is capable of retaining initial activity over a certain period of time. Also provided is a method for screening for an FAD-GDH suitable for use in CGM as well as a CGM device comprising an FAD-GDH.

4 Claims, 11 Drawing Sheets

Specification includes a Sequence Listing.

(56) References Cited

U.S. PATENT DOCUMENTS

| | | | |
|---|---|---|---|
| 2007/0267301 | A1 | 11/2007 | Sode |
| 2011/0318810 | A1 | 12/2011 | Tajima et al. |
| 2014/0154777 | A1 | 6/2014 | Sumida et al. |
| 2014/0287445 | A1 | 9/2014 | Tajima et al. |
| 2014/0287478 | A1* | 9/2014 | Sumida .............. C12Q 1/32 435/190 |
| 2015/0031059 | A1 | 1/2015 | Sumida et al. |
| 2015/0064733 | A1* | 3/2015 | Duefel .............. C12N 9/0006 435/14 |
| 2016/0319246 | A1 | 11/2016 | Araki |
| 2019/0002949 | A1* | 1/2019 | Guttman .............. C12Q 1/32 |
| 2019/0257781 | A1 | 8/2019 | Masakari |

FOREIGN PATENT DOCUMENTS

| | | | |
|---|---|---|---|
| JP | 2010-051312 A | 3/2010 | |
| JP | 2013-116102 A | 6/2013 | |
| JP | 2013-176363 A | 9/2013 | |
| JP | 2013-176364 A | 9/2013 | |
| JP | 2014-207911 A | 11/2014 | |
| JP | 2016-116488 A | 6/2016 | |
| JP | 2016-208915 A | 12/2016 | |
| JP | 2017-000137 A | 1/2017 | |
| WO | WO 02/36779 A1 | 5/2002 | |
| WO | WO 2012/169512 A1 | 12/2012 | |
| WO | WO 2013/022074 A1 | 2/2013 | |
| WO | WO 2013/051682 A1 | 4/2013 | |
| WO | WO 2013/164477 A1 | 11/2013 | |
| WO | WO 2015/099112 A1 | 7/2015 | |
| WO | WO 2015/129475 A1 | 9/2015 | |

OTHER PUBLICATIONS

Tchan-Gi Bak, Studies on glucose dehydrogenase of aspergillus oryzae: III. General Enzymatic Properties, 1967, Biochimica et Biophysica Acta (BBA)—Enzymology, vol. 146, Issue 2, pp. 317-327 (Year: 1967).*

"GLD3 Product Information sheet" is a pdf from Apr. 2015 accessible at https://fnkprddata.blob.core.windows.net/domestic/data/datasheet/BZL/GLD3.pdf obtained from https://www.funakoshi.co.jp/contents/63302 on May 29, 2022 (Year: 2015).*

Masakari et al., "Development of FAD-Dependent Glucose Dehydrogenase for CGM Sensor," poster/abstract of presentation made at the American Diabetes Association 77$^{th}$ Scientific Sessions, Jun. 11, 2017 (published Jun. 2, 2017), 5 pages.

Supplementary European Search Report dated Nov. 6, 2020 in EP 18775770.3.

Teymourian et al., "Electrochemical glucose sensors in diabetes management: an updated review (2010-2020)," Chemical Society Reviews, Jan. 1, 2020, DOI:10.1039/d0cs00304b, 39 pages.

Frias et al., "Review of Adverse Events Associated With False Glucose Readings Measured by GDH-PQQ-Based Glucose Test Strips in the Presence of Interfering Sugars," Diabetes Care, Apr. 2010, 33(4):728-729.

Gouda et al., "Thermal Inactivation of Glucose Oxidase," The Journal of Biological Chemistry, Jul. 4, 2003, 278(27):24324-24333.

Masakari et al., "Development of FAD-Dependent Glucose Dehydrogenase for CGM Sensor," poster/abstract of presentation made at the American Diabetes Association 77$^{th}$ Scientific Sessions, Jun. 11, 2007, 5 pages.

Ozawa et al., "Identification and characterization of thermostable glucose dehydrogenases from thermophilic filamentous fungi," Appl. Microbiol. Biotechnol., 2017 (Aug. 2016 online), 101:173-183.

Satake et al., "Novel glucose dehydrogenase from *Mucorprainii*: Purification, characterization, molecular cloning and gene expression in *Aspergillus sojae*," Journal of Bioscience and Bioengineering, Nov. 2015 (Apr. 23, 2015 online), 120(5):498-503.

Yamazaki et al., "Construction and Characterization of Direct Electron Transfer-Type Continuous Glucose Monitoring System Employing Thermostable Glucose Dehydrogenase Complex," Analytical Letters, Nov. 5, 2008, 41(13):2363-2373.

Lee et al., "Continuous glucose monitoring systems—Current status and future perspectives of the flagship technologies in biosensor research," Biosensors and Bioelectronics, 2021, 181:113054, 19 pages.

Office Action and Search Report dated Oct. 25, 2022 in CN 201880020927.8.

Hamza et al., "Enhancing long-term thermal stability in mesophilic glutamate dehydrogenase from Clostridium symbiosum by eliminating cysteine residues," Enzyme and Microbial Technology, 2007, 41:706-710.

Office Action and Search Report dated Jul. 8, 2023 in CN 201880020927.8.

* cited by examiner

CONTINUOUS GLUCOSE MONITORING USING AN FAD-DEPENDENT GLUCOSE DEHYDROGENASE

CROSS-REFERENCE TO RELATED APPLICATIONS

This application is the U.S. National Stage of PCT/JP2018/013830, filed Mar. 30, 2018, which claims priority to U.S. Provisional Application No. 62/479,442, filed Mar. 31, 2017.

The instant application contains a Sequence Listing which has been submitted in ASCII format via EFS-WEB and is hereby incorporated by reference in its entirety. Said ASCII copy, created on Jan. 16, 2019, is named sequence.txt and is 34 KB.

TECHNICAL FIELD

The present invention relates to continuous glucose monitoring using an FAD-Dependent glucose dehydrogenase.

BACKGROUND ART

Continuous glucose monitoring (CGM, also referred to as flash glucose monitoring, FGM) systems are important for diagnosing and managing diabetes. CGM systems are capable of measuring blood glucose levels over a period of from a few days to about 1-2 weeks. A CGM system comprises a glucose sensor.

Measurement of glucose levels may be carried out with a glucose oxidase (GOD). Glucose oxidase uses oxygen as the electron acceptor when oxidizing glucose. This may be affected by dissolved oxygen present in a measurement sample. Currently, to the best of our knowledge, commercially available CGM devices are all based on glucose oxidase (GOD). Certain GODs, such as GODs from microorganisms belonging to the genus *Aspergillus*, such as *Aspergillus niger*, are known to retain enzyme activity even when placed under harsh thermal conditions (Non-patent literature 1: THE JOURNAL OF BIOLOGICAL CHEMISTRY Vol. 278, No. 27, Issue of July 4, pp. 24324-24333, 2003). For this reason, CGM systems, in general, employ heat stable GODs.

Patent literature document 1 (WO 2015/099112, US20160319246) describes a GDH from a microorganism belonging to the genus *Mucor*.

Non-patent literature 2 (Satake, et al, J Biosci Bioeng. 2015 November; 120(5):498-503) describes an FAD-GDH from *Mucor prainii*. This document states that "Glucose oxidase (GOD) (EC 1.1.3.4) has been widely used as a mediated amperometric glucose sensor based on its high thermostability and high glucose selectivity".

Patent literature document 2 (WO 2002/036779, US 2004/0023330) describes a GDH from *Burkholderia cepacia*. The disclosed GDH is a membrane bound protein and comprises a cytochrome c domain. The amino acid sequence of the *B. cepacia* GDH is not similar to the FAD-dependent GDHs (also referred to herein as FAD-GDH) from microorganisms belonging to the genus *Mucor*.

Patent literature document 3 (WO2013/051682) describes a GDH from *Mucor guilliermondii* (MgGDH).

Patent literature document 4 (JP Patent Application publication (Kokai) No. 2013-116102) describes a GDH from *Mucor hiemalis* (MhGDH).

Patent literature document 5 (WO 2013/022074, US20140154777) describes CsGDH from *Circinella simplex* and CRGDH from *Circinella sp*.

Patent literature document 6 (JP Patent Application publication (Kokai) No. 2013-176363) describes MdrGDH from *Mucor* RD056860.

Patent literature document 7 (JP Patent Application publication (Kokai) No. 2013-176364) describes MsGDH from *Mucor subtilissimus*.

Patent literature document 8 (WO 2012/169512, US20140287445) describes a GDH from *M. prainii*.

Patent literature document 9 (WO 2015/129475, EP3112461) describes a GDH from *M. prainii*.

Patent literature document 10 (JP Patent Application publication (Kokai) No. 2014-207911) described a PQQ dependent GDH. The PQQ dependent GDH disclosed is reported to have activity on maltose.

Difficulties in implementing glucose sensors based on PQQ dependent GDHs have been reported. One reason is the relatively low substrate specificity, i.e., PQQ dependent GDHs are known to react on maltose in addition to glucose. See Non-patent literature 3.

CITATION LIST

Patent Literature

[PTL 1]
WO 2015/099112 (US20160319246)
[PTL 2]
WO 2002/036779 (US 2004/0023330)
[PTL 3]
WO 2013/051682
[PTL 4]
JP Patent Application publication (Kokai) No. 2013-116102 (U.S. Pat. No. 9,260,699)
[PTL 5]
WO 2013/022074 (US20140154777)
[PTL 6]
JP Patent Application publication (Kokai) No. 2013-176363
[PTL 7]
JP Patent Application publication (Kokai) No. 2013-176364
[PTL 8]
WO 2012/169512 (US20140287445)
[PTL 9]
WO 2015/129475 (EP3112461)
[PTL 10]
JP Patent Application publication (Kokai) No. 2014-207911

Non Patent Literature

[NPL 1]
THE JOURNAL OF BIOLOGICAL CHEMISTRY Vol. 278, No. 27, Issue of July 4, pp. 24324-24333, 2003
[NPL 2]
Satake, et al, J Biosci Bioeng. 2015 November; 120(5):498-503
[NPL 3]
Review of Adverse Events Associated With False Glucose Readings Measured by GDH-PQQ-Based Glucose Test Strips in the Presence of Interfering Sugars", Diabetes Care. 2010 April; 33(4): 728-729

SUMMARY OF INVENTION

Technical Problem

It is an object of the invention to provide an improved CGM method.

Solution to Problem

Continuous glucose monitoring can, in theory, be carried out with a glucose sensor comprising a glucose dehydrogenase (GDH) or a glucose oxidase (GOD). Glucose dehydrogenase uses an electron acceptor when dehydrogenizing glucose. This may be advantageous in that the measurement may not affected by dissolved oxygen.

However, to the best of the inventor's knowledge, currently available commercial CGM devices are all based on glucose oxidase (GOD). This is believed to be due to the thermal stability of the GODs. Certain GODs, such as GODs from microorganisms belonging to the genus *Aspergillus*, such as *Aspergillus niger*, are widely known to retain enzyme activity even when placed under harsh thermal conditions for a short period of time (see Non-patent literature 1). It was known that GODs retain higher activity when placed under harsh thermal conditions than GDHs, particularly in the case of enzymes suitable for glucose sensors. This indicates that GODs are more stable than GDHs are.

However, the present inventor surprisingly found that certain FAD-dependent glucose dehydrogenases retain higher enzyme activity at ambient temperatures over a long period of time compared to commercially available GODs under identical conditions. This was particularly surprising in view of the fact that the commercially available GODs retained higher enzyme activity compared to said FAD-dependent glucose dehydrogenases when placed under high temperatures, e.g., under an accelerated test comprising heat treatment.

In view of such findings, provided herein is a method of continuous glucose monitoring (CGM) comprising using an FAD-GDH. The FAD-GDH is capable of retaining initial activity over a certain period of time. Also provided herein is a method for screening for an FAD-GDH suitable for use in CGM as well as a CGM device comprising an FAD-GDH.

The following exemplary embodiments are provided:

Embodiment 1

A method of continuous glucose monitoring comprising using a GDH capable of
(a) retaining about 60% or more of the initial activity over a period of 1 week when retained at about 37-40° C.,
(b) retaining about 40% or more of the initial activity over a period of 2 weeks when retained at about 37-40° C., or
(c) retaining about 30% or more of the initial activity over a period of 3 weeks when retained at about 37-40° C.,
wherein said GDH is an FAD dependent GDH and wherein said GDH is not a membrane bound protein.

Embodiment 2

The method of embodiment 1, wherein the GDH is capable of retaining the activity specified in (a) to (c) of embodiment 1 when retained at a pH of 7.4.

Embodiment 3

The method of embodiment 1 or 2, wherein continuous glucose monitoring can be carried out without re-calibration.

Embodiment 4

A method for screening a GDH to be used in continuous glucose monitoring, said method comprising the steps of:
(i) preparing a candidate GDH,
(ii) retaining said candidate GDH at about 30-40° C. for a predetermined period,
(iii) determining the residual activity of said GDH after step (ii),
(iv) comparing the residual activity determined in step (iii) with the initial activity of said candidate GDH, wherein, when the residual GDH activity is
(a) about 60% or more compared to the initial GDH activity when retained at about 30-40° C. over a period of 1 week,
(b) about 40% or more compared to the initial GDH activity when retained at about 30-40° C. over a period of 2 weeks, or
(c) about 30% or more compared to the initial GDH activity when retained at about 30-40° C. over a period of 3 weeks,
then said candidate GDH is selected as a GDH having the potential to be used in continuous glucose monitoring over a period of 1 to 3 weeks.

Embodiment 5

The method of embodiment 4 in which step (ii) is not replaced with an accelerated heat treatment step comprising heat treatment at a temperature of about 50-60° C. at about 5-30 minutes.

Embodiment 6

A continuous glucose monitoring device comprising a GDH capable of
(a) retaining about 60% of the initial activity over a period of 1 week when retained at about 37-40° C.,
(b) retaining about 40% of the initial activity over a period of 2 weeks when retained at about 37-40° C., or
(c) retaining about 30% of the initial activity over a period of 3 weeks when retained at about 37-40° C., wherein said GDH is an FAD dependent GDH and wherein said GDH is not a membrane bound protein.

Embodiment 7

The device of embodiment 6, wherein the GDH is capable of retaining the activity specified in (a) to (c) of embodiment 6 when retained at a pH of 7.4.

Embodiment 8

The method of any one of embodiments 1-3, wherein the GDH has the following characteristics:
(1) activity as defined in any one of (a) to (c) of embodiment 1,
(2) substrate specificity: the reactivity to maltose is 2% or less, relative to the reactivity to D-glucose (100%);
(3) optimal activity pH: 6.5 to 7.5; and (4) a molecular weight of about 65 to about 81 kDa when measured by SDS-PAGE.

Embodiment 9

The method of any one of embodiments 1-5 and 8, wherein the GDH is from a microorganism belonging to the genus *Mucor, Absidia, Actinotnucor, Circinella, Parasitella* or *Rhizopus*.

Embodiment 10

The method of embodiment 9, wherein the GDH is a GDH from *Mucor prainii, Mucor circinelloides, Mucor circinelioides* f. *cirinelloides, Mucor ambiguus, Mucor hiemalis, Mucor hiemalis* f. *silvaticus, Mucor subtilissimus, Mucor guilliermondii, Mucor javanicus, Mucor dimorphosporus, Mucor* RD056860, *Mucor subtilissimus, Absidia cylindrospora, Absidia hyalospora, Actinomucor elegans, Circinella minor, Circinella mucoroides, Circinella muscae, Circinella rigida, Circinella simplex, Circinella umbellata, Parasitella parasitica* or *Rhizopus microsporus*.

Embodiment 11

The device of embodiment 6 or 7, wherein the GDH has the following characteristics:
(1) activity as defined in any one of (a) to (c) of embodiment 6,
(2) substrate specificity: the reactivity to maltose is 2% or less, relative to the reactivity to D-glucose (100%);
(3) optimal activity pH: 6.5 to 7.5; and
(4) a molecular weight of about 65 to about 81 kDa when measured by SDS-PAGE.

Embodiment 12

The device of embodiment 6, 7 or 11, wherein the GDH is from a microorganism belonging to the genus *Mucor, Absidia, Actinotnucor, Circinella, Parasitella* or *Rhizopus*.

Embodiment 13

The device of embodiment 12, wherein the GDH is a GDH from *Mucor prainii, Mucor circinelloides, Mucor circinelioides* f. *cirinelloides, Mucor ambiguus, Mucor hiemalis, Mucor hiemalis* f. *silvaticus, Mucor subtilissimus, Mucor guilliermondii, Mucor javanicus, Mucor dimorphosporus, Mucor* RD056860, *Mucor subtilissimus, Absidia cylindrospora, Absidia hyalospora, Actinomucor elegans, Circinella minor, Circinella mucoroides, Circinella muscae, Circinella rigida, Circinella simplex, Circinella umbellata, Parasitella parasitica* or *Rhizopus microsporus*.

Advantageous Effects of Invention

An advantage of the present invention over conventional devices using GODs is that GDHs can be used with but less frequently or without fingerstick calibrations over the sensor's lifetime due to the long-term stability thereof. Most systems based on GOD require calibration once in every certain period of time, such as once in every 12 hours, during the sensor's lifetime. One of the reasons for this is that GOD activity diminishes rapidly during incubation at ambient temperatures (30-40° C.), the temperature at which CGM devices are used. By contrast, it was found by the present inventor that, surprisingly, GDH retains higher stability (enzyme activity) at ambient temperatures (30-40° C.) over a long period of time such as 1-3 weeks and can be used without re-calibration or with re-calibration but less frequently.

Figure 1:
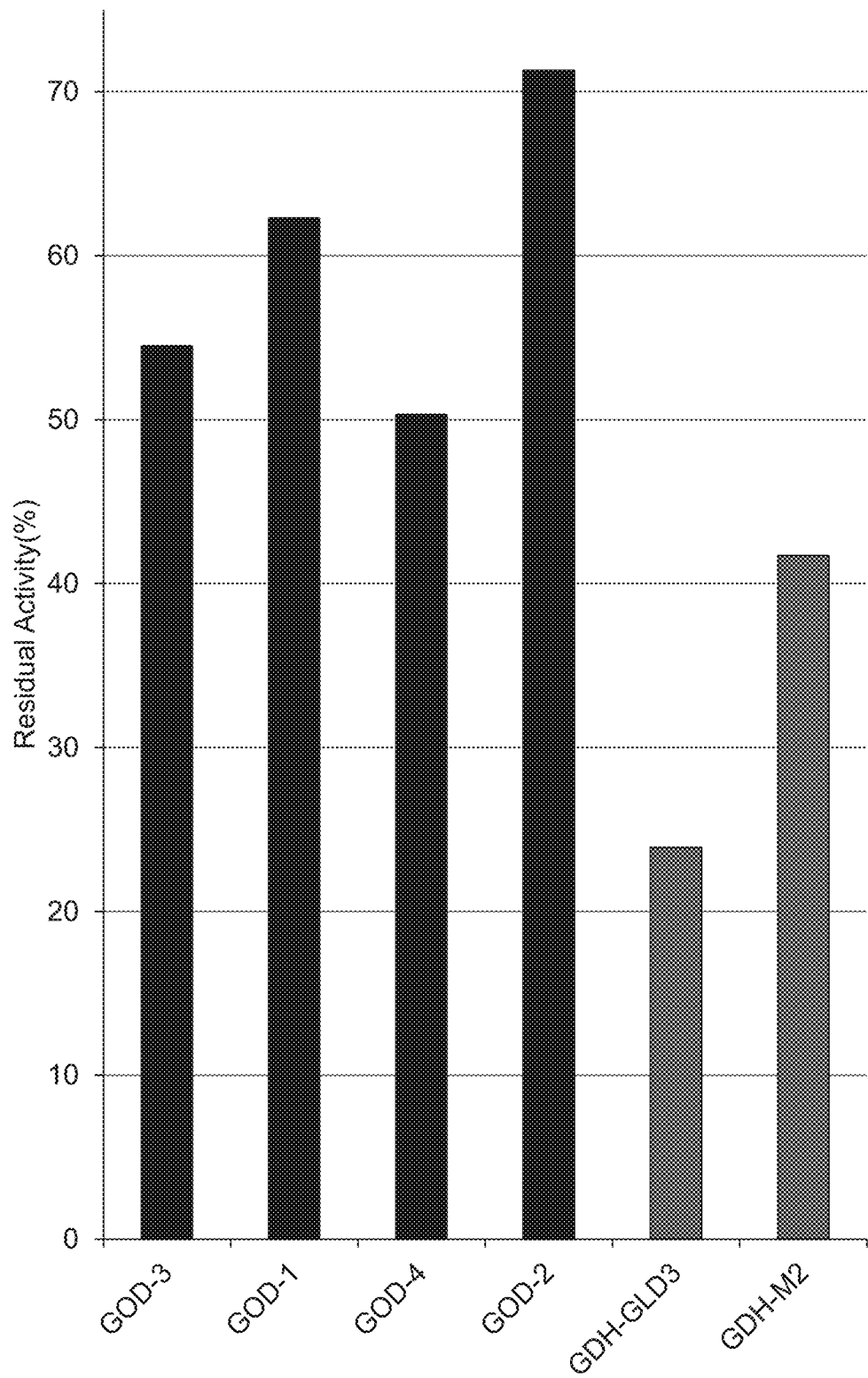
FIG. 1 shows residual enzyme activity of different types of GDH and GOD after heat treatment at 57° C. for 15 minutes.

DESCRIPTION OF EMBODIMENTS 1-1. Glucose Dehydrogenase Activity and Storage Stability In one embodiment, the present invention provides a method of continuous glucose monitoring (CGM) comprising using a GDH. In said method, a GDH capable of
(a) retaining about 60% or more, e.g., about 65% or more, about 70% or more, about 75% or more, about 80% or more, e.g., about 60-100%, about 60-99%, about 70-100%, 75-100%, or 80-100% of the initial activity for a period of 1 week when retained at about 37-40° C.,
(b) retaining about 40% or more, e.g., about 45% or more, about 50% or more, about 55% or more, about 60% or more, about 65% or more, e.g., about 40-100%, about 40-99%, about 45-100%, about 50-100%, about 55-100%, about 60-100%, or about 65-100% of the initial activity for a period of 2 weeks when retained at about 37-40° C., or
(c) retaining about 30% or more, e.g., about 35% or more, about 40% or more, about 45% or more, about 50% or more, about 55% or more, about 60% or more, e.g., about 30-100%, about 30-99%, about 40-100%, 45-100%, 50-100%, 55-100%, or about 60-100% of the initial activity for a period of 3 weeks when retained at about 37-40° C. may be used. Retaining GDH activity as above may be referred to herein as having (comprising) "storage stability". However, the term "storage" here is merely used for convenience and should not be construed or interpreted in any limiting way. That is, the phrase "storage stability" is merely intended to explain a characteristic of the GDH, namely, that the GDH retains activity over a certain period of time at a certain temperature, and does not imply that the GDH should be physically stored or shelved. The GDH having the storage stability described above can be used in an electrode, a glucose sensor, or a CGM device or in a method comprising continuous glucose monitoring. In one embodiment, said GDH may be an FAD-dependent GDH. In one embodiment, said GDH may be a soluble type GDH or derived from a soluble type GDH. The phrase "soluble type GDH" herein refers to a GDH which is soluble in solution and is not a membrane bound protein (such as the *B. cepacia* GDH described in WO 2002/036779, US 2004/0023330). It should be noted however, that the phrase "soluble type GDH" herein merely describes the "type" of GDH (or the origin of the GDH) and does not indicate that the GDH must physically be in solution. The soluble type GDH may be stored in dry state or immobilized onto an electrode. The type of such immobilized GDH may still be referred to herein as soluble type. In another embodiment, said GDH is not a membrane bound protein and does not comprise a cytochrome domain. In another embodiment, said GDH is not an FAD-GDH composed of three subunits capable of forming a complex non-covalently. The FAD-GDH from *B. cepacia* (WO 2002/036779, US 2004/0023330) is composed of three subunits capable of forming a complex non-covalently and this *B. cepacia* GDH is excluded from the GDHs used in the present methods and devices. In another embodiment, said GDH of the present invention is composed of one subunit, although this does not exclude the possibility of being fused covalently to one or more a cytochrome domains. In yet another embodiment, said GDH is not a PQQ-dependent GDH. In yet another embodiment, said GDH is not a NAD dependent GDH. In one embodiment, said GDH is a monomer. In one embodiment, said GDH is not a dimer. In one embodiment, the storage stability of the GDH may be assessed at a pH of about 7.0 to 7.5, e.g., about pH 7.4.

The GDH may retain activity as described in (a) to (c) above at a temperature of about 37-40° C., e.g., about 37° C., about 38° C., about 39° C., or about 40° C.

Preferably, a GDH relatively stable under harsh temperature conditions may be used. In one embodiment, a GDH which retains about 20% or more, e.g., about 20-100%, of its initial GDH activity after 15 minutes of heat treatment of at 57° C., pH 7.0 may be used.

In one embodiment, the GDH may be from a microorganism belonging to the genus *Mucor, Absidia, Actinotnucor* and *Circinella*. In another embodiment, the GDH may be a GDH from *Mucor prainii, Mucor circinelloides, Mucor circinelioides* f. *cirinelloides, Mucor ambiguus, Mucor hiemalis, Mucor hiemalis* f. *silvaticus, Mucor subtilissimus, Mucor guilliermondii, Mucor javanicus, Mucor dimorphosporus, Mucor* RD056860, *Mucor subtilissimus, Absidia cylindrospora, Absidia hyalospora, Actinomucor elegans, Circinella minor, Circinella mucoroides, Circinella muscae, Circinella rigida, Circinella simplex, Circinella umbellata, Parasitella parasitica* or *Rhizopus microsporus*. In another embodiment, the GDH may comprise mutations which alter characteristics thereof.

In one embodiment, the GDH used in the CGM method of the present invention may retain a higher enzyme activity over a long period of time such as 1-3 weeks compared to known GODs currently being used in conventional CGM systems. The residual activity ratio of a GDH or GOD enzyme is defined herein as follows:

Residual activity ratio=(residual activity $A$ after 3 weeks at about 37-40° C.)/(initial activity $B$)×100

Residual activity and initial activity of the same enzyme should be measured under identical assay conditions. In one embodiment, the residual activity and initial activity may be measured at a pH suitable for CGM such as pH 6.9 to 7.4, e.g., pH 7.0.

The pH of the CGM method may be adjusted to about 6.9 to 7.4, e.g., about 7.0. This is because the pH of blood is about 7.0. The pH may be adjusted using a phosphate buffer such as PBS or other conventional buffers.

In one embodiment, the residual activity ratio of the GDH used in the present invention is preferably higher than that of a known GOD enzyme used in a CGM system. Such known GOD enzyme may be a GOD from a microorganism belonging to the genus *Aspergillus* such as *Aspergillus niger* or *Aspergillus* sp. Such known GOD enzyme may be selected from the group consisting of Toyobo GOD (catalogue No. GLO-201, from *Aspergillus* sp.), Wako Pure Chemicals GOD (catalogue No. 074-02401, from *Aspergillus niger*), Sigma-Aldrich GOD type VII (GOD from *Aspergillus niger*), and Sigma-Aldrich GOD type X-S (GOD from *Aspergillus niger*).

In one embodiment, continuous glucose monitoring can be carried out with or without re-calibration. In an embodiment, continuous glucose monitoring can be carried out infrequently, e.g., with re-calibration once in every 1, 2, 3, 4, 5, 6, 7, 8, 9, 10, 11, 12, 13 or 14 days.

In another embodiment, the present invention provides a method for screening a GDH capable of being used in continuous glucose monitoring. This method comprises the steps of:

(i) preparing a candidate GDH, (ii) retaining said candidate GDH at about 30-40° C., e.g., about 37-40° C. for a predetermined period, (iii) determining the residual activity of said GDH after step (ii), and (iv) comparing the residual activity determined in step (iii) with the initial activity of said candidate GDH. When the residual GDH activity is (a) about 60% or more, e.g., about 65% or more, about 70% or more, about 75% or more, about 80% or more, e.g., about 60-100%, about 60-99%, about 70-100%, 75-100%, or 80-100% compared to the initial GDH activity when retained at about 30-40° C., e.g., about 37-40° C. for a period of 1 week, (b) about 40% or more, e.g., about 45% or more, about 50% or more, about 55% or more, about 60% or more, about 65% or more, e.g., about 40-100%, about 40-99%, about 45-100%, about 50-100%, about 55-100%, about 60-100%, or about 65-100% compared to the initial GDH activity when retained at about 30-40° C., e.g., about 37-40° C. for a period of 2 weeks, or (c) about 30% or more, e.g., about 35% or more, about 40% or more, about 45% or more, about 50% or more, about 55% or more, about 60% or more, e.g., about 30-100%, about 30-99%, about 40-100%, 45-100%, 50-100%, 55-100%, or about 60-100% compared to the initial GDH activity when retained at about 30-40° C., e.g., about 37-40° C. for a period of 3 weeks, then said candidate GDH can be selected as a GDH suitable for continuous glucose monitoring or as a GDH having the potential to be used in CGM, e.g., in CGM for over a period of 1 to 3 weeks. In step (ii) above, the candidate GDH may be retained at about 30-40° C., e.g., about 37-40° C. for a period of e.g., 0.5, 1, 2, 3, 4, 5, 6 or 12 hours, 1, 2, 3, 4, 5, 6 or 7 days, or 1, 2 or 3 weeks, when carrying out the screening. CGM is typically carried out at temperatures of about 30-40° C., in part since the average body temperature is about 37° C. Thus, screening of the GDH may be carried out at about 30-40° C., e.g., about 37-40° C., about 30° C., about 31° C., about 32° C., about 33° C., about 34° C., about 35° C., about 36° C., about 37° C., about 38° C., about 39° C., or about 40° C.

The candidate GDH may be a GDH from a microorganism belonging to the genus *Mucor*, or a derivative, variant or mutant thereof. The candidate GDH may be a GDH having low specificity towards maltose, D-galactose and/or D-xylose. The candidate GDH may be a heat stable GDH (thermally stable GDH), although it is not required to be more heat stable than GODs used in CGM devices under accelerated test conditions. In one embodiment, the candidate GDH of step (i) preferably retains about 20% or more, e.g., about 20-100%, of its initial GDH activity after 15 minutes of heat treatment of at 57° C., pH 7.0.

In order to screen for a GDH having the potential to be used in CGM, it may appear feasible according to conventional wisdom to carry out an accelerated heat treatment step on the candidate GDH enzymes instead of carrying out a full term a stability test over the entire lifetime of a CGM device, such as over 1-3 weeks. However, the present inventor surprisingly found that multiple GDHs retain higher stability at ambient temperatures over a long period of time compared to commercially available GODs under similar conditions. This was particularly surprising in view of the fact that known GODs retained higher activities than GDHs in accelerated tests employing heat treatment at 57° C. Therefore, in one embodiment of the present invention, it may be preferable not to replace step (ii) above with an accelerated test comprising a heat treatment step such as heat treatment at a temperature of about 50-60° C., at about 5-30 minutes.

In one embodiment, the present invention provides a continuous glucose monitoring device comprising a GDH capable of (a) retaining 60% or more, e.g., about 65% or more, about 70% or more, about 75% or more, about 80% or more, e.g., about 60-100%, about 60-99%, about 70-100%, 75-100%, or 80-100% of the initial activity for a period of 1 week when retained at about 37-40° C., (b) retaining 40% or more, e.g., about 45% or more, about 50% or more, about 55% or more, about 60% or more, about 65% or more, e.g., about 40-100%, about 40-99%, about 45-100%, about 50-100%, about 55-100%, about 60-100%, or about 65-100% of the initial activity for a period of 2 weeks when retained at about 37-40° C., or (c) retaining 30% or more, e.g., about 35% or more, about 40% or more, about 45% or more, about 50% or more, about 55% or more, about 60% or more, e.g., about 30-100%, about 30-99%, about 40-100%, 45-100%, 50-100%, 55-100%, or about 60-100% of the initial activity for a period of 3 weeks when retained at about 37-40° C., wherein said GDH is an FAD dependent GDH and wherein said GDH is not a membrane bound protein. In one embodiment, said GDH is not a PQQ dependent GDH.

In terms of monitoring glucose over a certain time period, continuous glucose monitoring (CGM) may also be referred to as flash glucose monitoring (FGM). As such, the phrase "continuous glucose monitoring", as used herein with regard to embodiments of the present invention, encompass embodiments of flash glucose monitoring, unless clearly indicated otherwise.

In one embodiment, the device comprises a GDH which preferably retains about 20% or more, e.g., about 20-100%, of its initial GDH activity after 15 minutes of heat treatment of at 57° C., pH 7.0.

In one embodiment, the CGM device may comprise a glucose sensor to be placed under the skin. The sensor may be worn for a certain time period such as from one day to about 3 weeks. The sensor portion may be disposable. The sensor may comprise a sensor membrane layer to prevent direct tissue contact with the enzyme. The sensor may be designed to be inserted into the abdomen by using an applicator. In one embodiment, the present invention provides a CGM device further comprising a transmitter and a link from the sensor to the transmitter. The transmitter need not be implanted. Preferably, the transmitter is capable of communicating to a radio receiver. The CGM device may further comprise an electronic receiver that may continuously display glucose levels. The CGM device may optionally comprise a fingerstick (fingerprick) for calibration. The CGM device may optionally comprise a manual for use. In one embodiment, the CGM device may be self-powered (SPGS) and the reference electrode may be omitted.

FAD-GDH catalyzes a reaction in which the hydroxyl group of glucose is oxidized in the presence of an electron acceptor to form glucono-δ-lactone.

This reaction can be used to measure the activity of an FAD-GDH, for example, by using the following system that utilized phenazine methosulfate (PMS) and 2,6-dichloroindophenol (DCIP) as electron acceptors.

D-glucose+PMS (oxidized form)→D-glucono-δ-lactone+PMS (reduced form) (catalyzed by FAD-GDH)     (Reaction 1)

PMS (reduced form)+DCIP (oxidized form)→PMS (oxidized form)+DCIP (reduced form)     (Reaction 2)

In Reaction 1, glucose is oxidized and reduced form PMS is produced. In subsequent Reaction 2, the reduced form PMS is oxidized and DCIP is reduced. By detecting the degree of decrease in oxidized form DCIP, by way of change in optical absorbance at a wavelength of 600 nm, GDH enzyme activity can be determined.

Activity of FAD-GDH can be measured as follows. 2.05 mL of 100 mM phosphate buffer (pH 7.0), 0.6 mL or 1 M D-glucose solution and 0.15 mL of 2 mM DCIP solution are mixed and then incubated at 37° C. for 5 minutes. Then, 0.1 mL of 15 mM PMS solution and 0.1 mL of enzyme sample solution are added to initiate the reaction. Optical absorbance is measured at the initial conditions and over time, decrease in optical absorbance at 600 nm (ΔA600) per minute is determined, and GDH activity can be computed accordingly. 1 U of GDH activity can be defined as the amount of enzyme that reduces 1 μmol of DCIP in one minute in the presence of D-glucose at a concentration of 200 mM at 37° C.

$$\text{GDH activity (U/mL)} = \frac{-(\Delta A600 - \Delta A600_{blank}) \times 3.0 \times df}{16.3 \times 0.1 \times 1.0}$$

The value 3.0 in the equation represents the amount of the reaction reagent and enzyme reagent (mL), 16.3 represents the millimolar molecular extinction coefficient (cm²/μmol), 0.1 represents the amount of the enzyme solution (mL), 1.0 represents the cell length (cm), $\Delta 600_{blank}$ represents the amount of decrease in blank optical absorbance per minute at 600 nm where only the buffer is added to initiate the reaction instead of adding the enzyme solution, and df represents the dilution factor.

The GDH used in the present methods may have glucose dehydrogenase activity and storage stability as described above. Equivalents thereof may also be used.

1-2. Substrate Specificity

The GDH used in the present methods may have high substrate specificity. In one embodiment, the GDH may have low reactivity at least to maltose compared to the reactivity to glucose (D-glucose). In another embodiment, the GDH may have low reactivity at least to maltose and xylose (D-xylose), compared to the reactivity to glucose (D-glucose). In one embodiment, the GDH used in the present methods has reactivity to maltose of, for example, 2% or less, preferably 1% or less, more preferably 0.7% or less, more preferably 0.4% or less, relative to the reactivity to glucose at the same concentration (100%). In one embodiment, the GDH used in the present methods may have reactivity to xylose, for example, of 3% or less, more preferably 2% or less, more preferably 1 or less, more preferably 0.6% or less, relative to the reactivity to glucose at the same concentration (100%). In another embodiment, the GDH may have low reactivity at least to galactose, compared to the reactivity to glucose (D-glucose). In one embodiment, the GDH used in the present methods may have reactivity to galactose, for example, of 5% or less, 4% or less, 3% or less, 2% or less, or 1 or less, relative to the reactivity to glucose at the same concentration (100%).

Reactivity of GDH used in the present methods to each sugar can be measured by replacing glucose with another sugar such as xylose or maltose in the method for measuring the glucose dehydrogenase activity described herein, and comparing the measured activity with that obtained with glucose. For example, the concentration of each sugar can be set as 200 mM. Further, when reactivity to glucose is measured, the final enzyme concentration of the reaction liquid can be set as 1.4 µg/mL and when reactivity to xylose or maltose is measured, the final enzyme concentration of the reaction liquid can be set as 28 µg/mL. The GDH used in the present methods having such high substrate specificity can be used as an enzyme for accurately measuring the glucose concentration of a sample, for example, even when the sample contains impurities, such as maltose or xylose.

1-3. Optimal pH

The GDH used in the present methods may have a broad optimal pH activity range. Since CGM is carried out on blood and interstitial fluid, it is preferable for the GDH enzyme used in the method to have an optimal pH around neutral pH (pH 7.0). In one embodiment, the GDH used in the present methods may have, for example, optimal pH activity at a pH of from 5.0 to 7.5, preferably from 5.5 to 7.5, more preferably from 6.0 to 7.5, more preferably from 6.5 to 7.5. In another embodiment, the GDH used in the present methods may have optimal pH activity at a pH of from 5.0 to 8, preferably from 5.5 to 7.5, more preferably from 6.0 to 7.5, more preferably from 6.5 to 7.5. Such GDHs are shown in the examples. In one embodiment, optimal pH may be considered as a relative activity of 70% or more relative to the highest activity (100%). In another embodiment, optimal pH may be considered as a relative activity of 75% or more, for example 80% or more relative to the highest activity (100%). In one embodiment, the GDH used in the present methods has an optimal pH of 6.0 to 7.5 wherein optimal activity is 70% or more activity relative to the highest activity (100%).

Optical absorbance is measured at the initial conditions and over time, decrease in optical absorbance at 520 nm ($\Delta A520$) per minute is determined, and GDH activity can be computed accordingly. 6.8 represents the millimolar molecular extinction coefficient ($cm^2/\mu mol$). The molar adsorption coefficient of DCIP at 600 nm is known to vary to a large degree depending on the pH. The molar adsorption coefficient of DCIP at 520 nm is known to be fairly constant regardless of pH. Measurements can be made at 520 nm by taking this into account.

1-4. Optimal Activity Temperature

The GDH used in the present methods may have an optimal activity temperature over a broad range, for example, of 30 to 50° C., 30 to 55° C., 35 to 50° C., 35 to 55° C., 35 to 60° C., or 30 to 60° C. The optimal activity temperature of 30 to 60° C. herein typically means that the temperature is more or less within a range of about 30 to 60° C., and the range further includes an acceptable allowance to some extent, while the activity is optimal. In the present specification, optimal activity temperature can be computed by measuring the enzyme activity in a potassium phosphate buffer solution (pH of 7.0) at a final enzyme concentration of the reaction liquid (1.4 µg/mL).

1-5. pH Stability

The GDH used in the present methods may have high pH stability over a broad range of pH. In one embodiment, the GDH used in the present methods is stable at least within the entire pH range of 5.0 to 7.5. In the present specification, when 100 U/mL of enzyme that has been treated at 25° C. for 16 hours under specific pH conditions has residual enzyme activity of 75% or more compared to the initial enzyme activity of the same enzyme before treatment (100%), the enzyme is considered to be stable under such pH condition.

1-6. Temperature Stability

The GDH used in the present methods may have temperature stability. In one embodiment, the GDH used in the present methods is, for example, stable least at 50° C. or less (i.e., within a temperature range of 0 to 50° C.), 51° C. or less, 52° C. or less, 53° C. or less, 54° C. or less, 55° C. or less 56° C. or less, or 57° C. or less for 15 minutes. In the present specification, when 10 U/mL of enzyme that has been treated for 15 minutes in an appropriate buffer solution (e.g., potassium acetate buffer (pH of 5.0)) under specific temperature conditions has remaining enzyme activity of 20% or more compared to the initial enzyme activity of the same enzyme prior to heat treatment (100%), the enzyme is considered to be stable under such temperature condition.

The GDH used in the present methods may have at least one or more, 2 or more, 3 or more, 4 or more, 5 or more or all six of the enzyme characteristics described above. The GDH used in the present methods may have any combination of the characteristics described above. In one embodiment, that the GDH used in the present methods may have the characteristic described in Section 1-1, and further at least one characteristic selected from the group consisting of the characteristics described in Sections 1-2, 1-3, 1-4, 1-5, and 1-6 above.

1-7. Molecular Weight

In one embodiment, the polypeptide moiety constituting the GDH used in the present methods may have a molecular weight of about 65 to 81 kDa, about 65 to 80 kDa, about 65 to 75 kDa, about 65 to 70 kDa or about 70 kDa as measured by SDS-PAGE. The phrase "about 70 kDa as measured by SDS-PAGE" includes a range in which a person artisan would usually determine that the band is present at a position of 70 kDa when the molecular weight of the polypeptide is measured by SDS-PAGE. The skilled artisan will appreciate that the band appearing on an SDS-PAGE may vary 5 kD above or below the expected value depending on the conditions. "Polypeptide moiety" refers to the polypeptide moiety of GDH and does not include attached sugar chains.

In one embodiment, the polypeptide moiety constituting the GDH used in the present methods may have a theoretical molecular weight of about 65 to 80 kDa, about 65 to 75 kDa, about 65 to 70 kDa, about 69 to 70 kDa or about 70 kDa as deduced from the amino acid sequence. The phrase "theoretical molecular weight of about 70 kDa as deduced from the amino acid sequence" refers to the molecular weight of the GDH computed from the amino acid sequence. This does not include attached sugar chains.

When producing the GDH used in the present methods using certain microorganisms, the GDH maybe expressed in glycosylated form. In one embodiment, regarding glycosylated forms of GDH, heat treatment or deglycosylating treatment may be carried out to remove sugar chains to provide the polypeptide moiety. Deglycosylation may be carried out using a glycohydrolase such as EndoH endoglycosidase. When producing the GDH used in the present methods using certain other microorganisms, the GDH may be expressed in non-glycosylated form. For such form, the expressed GDH is the polypeptide moiety.

Various methods are known for removing sugar chains from glycosylated form GDHs. One example may be to denature the glycosylated GDH by heat treatment at 100° C. for 10 minutes, followed by treatment with the endoglycosidase Endo H at 37° C. for 14 hours. One example may be to denature the glycosylated GDH by treatment with the endoglycosidase Endo H at 37° C. for 24 hours.

Where the GDH used in the present method has attached sugar chains, the molecular weight thereof is not limited so long as there is no adverse effect on the glucose dehydrogenase activity, substrate specificity, specific activity, and the like. For example, when the GDH used in the present method has attached sugar chains, the molecular weight thereof may be 80 to 120 kDa as measured by SDS-PAGE. The GDH used in the present method may or may not be a glycosylated form. The molecular weight measurement by SDS-PAGE may be performed using conventional techniques and devices with the use of commercially available molecular weight markers.

In one embodiment, that the GDH used in the present methods may have the characteristic described in Section 1-1, and further at least one characteristic selected from the group consisting of the characteristics described in Sections 1-2 to 1-7 above.

1-8. Origin

The origin of the GDH used in the present methods is not particularly limited as long as the GDH has the characteristics described above. The GDH used in the present method can be derived from, for example, microorganisms belonging to members of the subphylum Mueoromyeotina, members of the class Mucoromycetes, members of the order Mucorales, members of the family Mucoraceae. Specific examples include *Mucor* species, *Absidia* species, *Actinotnucor* species and *Circinella* species. Examples of *Mucor* species include *Mucor prainii, Mucor javanicus, Mucor circinelioides* f. *cirinelloides, Mucor ambiguus, Mucor guilliermondii, Mucor hiemalis* f. *silvaticus, Mucor subtilissimus* and *Mucor dimorphosporous*. Examples of *Absidia* species include *Absidia cylindrospora* and *Absidia hyalospora*. Examples of *Actinomucor* species include *Actinomucor elegans*. Examples of *Circinella* species include *Circinella minor, Circinella mucoroides, Circinella muscae, Circinella rigida, Circinella simplex* and *Circinella umbellata*. Further examples include those described in WO2010/140431, US 2011/0318810. Further examples include *Parasitella parasitica* and *Rhizopus microsporus*.

Other origins may be the genus *Arthrinium* and the genus *Apiospora*. Examples of the genus *Arthrinium* include, but are not limited to, *Arthrinium japonicum, Arthrinium phaeospermum, Arthrinium terminalis, Arthrinium saccharicola, Arthrinium sacchari, Arthrinium serenense, Arthrinium arundinis, Arthrinium euphaubie*. Examples of the genus *Apiospora* include, but are not limited to, *Apiospora montagnei, Apiospora setosa*, and *Apiospora tintinnabula* and *Arthrinium sacchari*. For microorganisms of the genus *Arthrinium* and the genus *Apiospora*, see U.S. Pat. No. 9,796,963, incorporated herein in its entirety.

Other origins include, but are not limited to, members of the Metarhizium genus, for example, Metarhizium sp., for example, Metarhizium sp. F2114 (HyphaGenesis Inc.) (see JP Patent Application Publication No. 2016-116488, incorporated herein in its entirety); members of the *Aspergillus* genus, for example, *Aspergillus* sp. RD009469 (see WO 2015/060150, incorporated herein in its entirety), *Aspergillus iizukae*, for example *Aspergillus iizukae* No. 5453 strain (see WO 2017/077924, incorporated herein in its entirety), *Aspergillus versicolor*, for example *Aspergillus versicolor* No. 52439 strain (see JP Patent Application Publication No. 2017-221147, incorporated herein in its entirety); *Aspergillus kawachii, Aspergillus awamori*, e.g., *Aspergillus awamori* No. 1731 strain (see JP Patent Application Publication No. 2017-112860, incorporated herein in its entirety); *Aspergillus foetidus*, e.g., *Aspergillus foetidus* NBRC4312 strain (NBRC), *Aspergillus niger* CBS 513.88 strain (Centraalbureau voor Schimmelcultures: CBS), *Aspergillus awamori* No. 1751 strain, *Aspergillus aureus*, e.g., *Aspergillus aureus* No. 2062 strain (see JP Patent Application Publication No. 2017-112858, incorporated herein in its entirety), *Aspergillus bisporus*, e.g., *Aspergillus bisporus* NBRC32017 strain (NBRC); *Thermoascus aurantiacus*, e.g., *Thermoascus aurantiacus* strain 6766, *Thermoascus aurantiacus* strain 9748 (see JP Patent Application Publication No. 2015-167506, incorporated herein in its entirety); and *Talaromyces emersonii*, e.g., *Talaromyces emersonii* 31232 strain and 9734 strain, *Thermoascus crustaceus*, e.g., *Thermoascus crustaceus* 9129 strain and 9816 strain and other microorganisms disclosed in Table 1 of WO 2014/045912 (see WO 2014/045912, incorporated herein in its entirety) as well as Botryothinia fuckeliana (see WO 2012/001976, incorporated herein in its entirety).

In one embodiment, an FAD-GDH can be obtained, for example, by initially obtaining a known GDH gene such as the GDH gene described in Patent document 1 (WO 2015/099112, US20160319246), Patent document 8 (WO2012/169512, US20140287445) or Patent document 9 (WO 2015/129475, EP3112461). The obtained gene may or may not be mutated. Mutations may be any mutation such as those described in these documents or corresponding mutations. In one embodiment, the GDH from *Mucor prainii* (MpGDH, SEQ ID NO:1) may be modified by introducing mutations N66Y/N68G/C88A/Q233R/T387C/E554D/L557V/S559K thereto.

Other mutations may also be applied, such as mutations described in the literature. Amino acid substitutions may be indicated herein with the abbreviation "aXXXb" (wherein a is the amino acid prior to substitution, XXX is the position within a particular amino acid sequence being substituted and b is the amino acid post substitution). For example, A175C with regard to SEQ ID NO:1 represents the substitution where alanine at position 175 of SEQ ID NO:1 is replaced with cysteine.

In another embodiment, the GDH designated as GLD3 (Funakoshi) or equivalents thereof can be used in CGM. In another embodiment, a GDH derived from the *Mucor hiemalis* GDH can be used in CGM. In another embodiment, the GDH designated MpGDH-M2 (SEQ ID NO: 11) can be used in CGM.

Examples of methods for introducing target amino acid substitutions include methods in which a mutation is introduced randomly and methods in which a site-directed mutation is introduced at a designated position. Examples of Random mutagenesis methods include Error-Prone PCR Methods (Techniques, 1, 11-15 (1989)) and methods using XL1-Red competent cells, in which errors frequently occur during plasmid replication and which are susceptible to occurrence of modification during cell proliferation (Stratagene Corp.). Examples of site directed mutagenesis methods include methods comprising selecting an amino acid which may confer a target effect, and introducing a site-directed mutation using conventional kits such as the commercially available Quick Change Site-Directed Mutagenesis Kit (Stratagene Corp.).

In order to obtain an FAD-GDH gene, chromosomal DNA or mRNA can be extracted from known microbial cells or various other cells having the ability to produce FAD-GDH using conventional methods such as those described in Current Protocols in Molecular Biology, Wiley Interscience (1989)). Further, cDNA can be synthesized by using mRNA as a template. A chromosomal DNA or cDNA library can then be prepared using chromosomal DNA or cDNA so obtained.

Subsequently, DNA containing target gene fragments encoding FAD-GDH having high substrate specificity may be amplified, said DNA fragments may be connected, and DNA containing the entire FAD-GDH gene can be obtained. Connection of the DNA fragments may be carried out by synthesizing a suitable probe DNA based on amino acid sequence information of a known FAD-GDH, using the probe DNA to select an FAD-GDH gene having high substrate specificity from a chromosomal DNA or cDNA library, or using the polymerase chain reaction (PCR) method such as 5' RACE or 3' RACE by preparing suitable primer DNA based on the amino acid sequence and linking the DNA fragments.

A gene encoding FAD-GDH may be used as the starting material and screening of mutants can be carried out by selecting clones expressing preferable FAD-GDHs.

Mutants may be produced by exposing an FAD-GDH gene or cell comprising said gene to mutagens or to ultraviolet radiation, or carry out genetic engineering methods that cause mutagenesis.

Examples of mutagens include N-methyl-N'-nitro-N-nitrosoguanidine, hydroxylamine, nitrous acid, sulfurous acid, hydrazine, formic acid and 5-bromouracil among others. In the case of irradiating with ultraviolet light, irradiation can be carried out using conventional techniques as described in Chemistry Today, 24-30, June 1989.

Examples of site-specific mutagenesis include the Kunkel method (Proc. Natl. Acad. Sci. U.S.A., 82, 488 (1985); Methods Enzymol., 154, 367 (1987)), the Eckstein method (Nucleic Acids Res., 13, 8749 (1985); Nucleic Acids Res., 13, 8765 (1985); Nucleic Acids Res., 14, 9679 (1986)), and the Kramer method (Nucleic Acids Res., 12, 9441 (1984); Methods Enzymol., 154, 350 (1987); Gene, 37, 73 (1985)). Commercially available kits (such as the Transformer Mutagenesis Kit (Clontech Laboratories, Inc.), ExOIII/Mung Bean Deletion Kit (Stratagene Corp.) or Quick Change Site-Directed Mutagenesis Kit (Stratagene Corp.)) may be used to transform a DNA sequence.

Further, a FAD-GDH gene may be obtained by using DNA synthesis methods. The gene may be designed to comprise the gene sequence of a naturally occurring GDH or may have mutations.

The DNA sequence of a GDH gene may be sequenced using conventional sequencing techniques and commercially available systems such as the Multi-Capillary DNA Analysis System CEQ2000 (Beckman Coulter Inc.) may be used.

An FAD-GDH can be acquired by obtaining a naturally occurring FAD-GDH or by modifying a known FAD-GDH. Examples of microorganisms comprising an FAD-GDH include members of the subphylum Mueoromyeotina, members of the class Mucoromycetes, members of the order Mucorales, members of the family Mucoraceae. Specific examples include *Mucor* species, *Absidia* species, *Actinotnucor* species and *Circinella* species.

Examples of *Mucor* species include *Mucor prainii, Mucor javanicus, Mucor circinelioides* f. *cirinelloides, Mucor ambiguus, Mucor guilliermondii, Mucor hiemalis* f. *silvaticus, Mucor subtilissimus* and *Mucor dimorphosporous*. Examples of *Absidia* species include *Absidia cylindrospora* and *Absidia hyalospora*. Examples of *Actinomucor* species include *Actinomucor elegans*. Examples of *Circinella* species include *Circinella minor, Circinella mucoroides, Circinella muscae, Circinella rigida, Circinella simplex* and *Circinella umbellata*. Further examples include those described in WO2010/140431, US 2011/0318810. Further examples include *Parasitella parasitica* and *Rhizopus microsporus*. Further examples include those described above.

An FAD-GDH gene can be incorporated into a vector such as a bacteriophage, cosmid or plasmid and these can be used to transform a prokaryotic cell or eukaryotic cell using conventional methods.

Examples of prokaryotic host cells include microorganisms belonging to the genus *Escherichia* such as *Escherichia coli* strain K-12, *Escherichia coli* BL21(DE3), *Escherichia coli* JM109, *Escherichia coli* DH5α, *Escherichia coli* W3110 or *Escherichia coli* C600 (Takara Bio Inc.). Cells can be transformed or transduced using $CaCl_2$ methods or electroporation methods. Commercially available competent cells (such as ECOS Competent *Escherichia coli* BL21 (DE3), Nippon Gene Co., Ltd.) may be employed.

Examples of eukaryotic host cells include yeasts such as those of the genus *Zygosaccharomyces*, genus *Saccharomyces*, genus *Pichia* and genus *Candida*. Marker genes may be used to identify transformed cells.

Examples of marker genes include genes that complement the nutritional requirements of the host such as URA3 or TRP 1. Further, the inserted gene may comprise a promoter or other control sequence (such as an enhancer sequence, terminator sequence or polyadenylation sequence). Examples of promoters include the GAL1 promoter and ADH1 promoter. Yeast may be transformed using conventional methods such as, without limitation, the lithium acetate method (Methods Mol. Cell. Biol., 5, 255-269 (1995)) or electroporation method (J. Microbiol. Methods, 55, 481-484 (2003)). Alternatively, methods such as the spheroplast method or glass bead method may be used.

Further examples of eukaryotic host cells include molds such as those of *Aspergillus* species and *Tricoderma* species. The inserted gene may comprise a promoter, such as the tef1 promoter, and other control sequences (such as a secretion signal sequence, enhancer sequence, terminator sequence or polyadenylation sequence). Further, the inserted gene may also comprise a marker gene such as niaD or pyrG to select a transformed cell. Further, the inserted gene may comprise homologous recombination domains for insertion into the chromosome. Known methods such as the method described by Unkles et al., (Mol. Gen. Genet., 218, 99-104 (1989)) using polyethylene glycol and calcium chloride following protoplast formation may be employed to transform molds.

An FAD-GDH may be produced by culturing a host cell capable of producing FAD-GDH and collecting FAD-GDH from the culture.

Examples of media to culture the host cells include media comprising one or more types of inorganic salts such as sodium chloride, potassium dihydrogen phosphate, dipotassium hydrogen phosphate, magnesium sulfate, magnesium chloride, ferric chloride, ferric sulfide or manganese sulfate and one or more type of nitrogen source such as yeast extract, tryptone, peptone, beef extract, corn steep liquor, or soybean or wheat bran extract. The medium may further comprise carbohydrate sources or vitamins where necessary. The initial pH of the medium may be adjusted to a pH of 6 to 9 although not limited to this range.

Culturing may be carried out by aeration-agitation submerged culturing, shake culturing or static culturing for 1 hours to 4 days or more at a culturing temperature of e.g., 10-42° C., such as 25° C. or 37° C.

After culturing, the FAD-GDH may be collected from the culture. This may be carried out using conventional methods. In one example, microbial cells can be pulverized using ultrasonication or ground or milled, the enzyme can be extracted using a lytic enzyme such as lysozyme or yatalase, or the enzyme can be released from the cells by lysing the cells with agitation or exposing the cells to toluene. A crude FAD-GDH may then be obtained by filtering the solution, the solid fraction may be removed by centrifugation, nucleic acids may be removed with streptomycin hydrochloride, protamine sulfate or manganese sulfate where necessary, ammonium sulfate, alcohol or acetone may be used for fractionation and the precipitate may be collected.

The crude FAD-GDH enzyme can be purified using conventional means. Purification can be carried out using gel filtration methods using a gel such as Sephadex (Registered Trademark), Ultrogel (Registered Trademark) or Biogel (Registered Trademark), adsorption elution methods using ion exchange resins, electrophoresis methods using polyacrylamide gels, adsorption elution methods using hydroxyapatite, precipitation methods such as sucrose density gradient centrifugation, affinity chromatography methods, or fractionating methods using a molecular sieve membrane or hollow fiber membrane, or a combination thereof.

Measurement of glucose concentration can be carried out using a colorimetric glucose assay kit. A composition containing an FAD-GDH, an electron acceptor and a reaction accelerator can be used. Agents selected from the group consisting of N-(2-acetamido)iminodiacetic acid (ADA), bis(2-hydroxyethyl)iminotris(hydroxymethyl)methane (Bis-Tris), sodium carbonate and imidazole may be retained in the reaction layer of a glucose assay kit. Optionally, a pH buffer or coloring reagent may be added. A sample containing glucose is then added and reaction is allowed to take place for a certain amount of time. During reaction, optical absorbance is monitored.

The optical absorbance corresponds to an absorption wavelength, preferably to the maximum absorption wavelength of an electron acceptor that is discolored by reduction, or a pigment formed by polymerization as a result of accepting electrons from an electron acceptor.

Glucose concentration in the sample can be computed with reference to a calibration curve produced by using glucose solutions with known standard concentrations. In a rate change method, the concentration may be computed based on the rate of change in absorbance per unit time. In an endpoint method, the concentration may be computed based on the point at which all glucose in the sample has been consumed (oxidized).

In one example employing a mediator and a coloring reagent, glucose can be quantified by adding 2,6-dichloroindophenol (DCIP) as an electron acceptor followed by monitoring the decrease in absorbance at 600 nm. Further, glucose concentration can be computed by adding an electron acceptor in the form of phenazine methosulfate (PMS) and a coloring reagent in the form of nitrotetrazolium blue (NTB) followed by determining the amount of diformazan formed by measuring absorbance at 570 nm. Other electron acceptors and coloring reagents may of course be used.

Glucose Sensor Comprising FAD-GDH

In one embodiment, a glucose sensor comprising an FAD-GDH is provided. In one embodiment, the glucose sensor comprises a working electrode comprising the FAD-GDH, a reference electrode and a counter electrode. An electrode such as a carbon electrode, palladium electrode, gold electrode or platinum electrode may be used for the working electrode, and the FAD-GDH may be immobilized on the working electrode. The type of FAD-GDH to immobilize may be a soluble type FAD-GDH. Alternatively, or in addition, the electron mediator may be immobilized on the working electrode. The counter electrode may be a conventional electrode such as a platinum electrode or Pt/C electrode. The reference electrode may be a conventional electrode such as an Ag/AgCl electrode.

Examples of immobilization methods include methods using cross-linkers, methods comprising embedding in a polymer matrix, methods comprising covering with a dialysis membrane, and methods utilizing photo-cross-linkable polymers, electrically conductive polymers and oxidation-reduction polymers. Alternatively, the FAD-GDH may be immobilized in a polymer together with an electron mediator such as ferrocene or a derivative thereof, immobilized by adsorbing onto the electrode, or a combination thereof. In a typical method, the FAD-GDH may be immobilized on a carbon electrode using glutaraldehyde followed by blocking of glutaraldehyde using a reagent comprising an amino group. Another method may be to use polyethylene glycol diglycidyl ether (PEGDE) as the cross-linker. The molecular weight of PEGDE is not limited and any type may be used.

Methods for producing a glucose sensor can be found in the literature, such as Liu, et. al, Anal. Chem. 2012, 84, 3403-3409 and Tsujimura, et. al, J. Am. Chem. Soc. 2014, 136, 14432-14437 (both incorporated by reference in their entirety). Disclosed methods may be modified by using a GDH in place of GOD. For example, a redox polymer, such as a polymer containing an osmium complex can be mixed with another polymer such as polyethylene glycol and a GDH in a suitable buffer such as HEPES buffer to prepare a glucose sensing reagent. The osmium complex may be an osmium complexed with one or several organic molecules including a bipyridine molecule such as 2,2'-bipyridine, a biimidazole molecule such as 2,2'-biimidazole, a pyridine-imidazole compound such as 2-(2-pyridyl)imidazole or combinations thereof. The organic molecules which form the complex may optionally be substituted with an alkyl group, such as a $C_1$-$C_6$ alkyl, such as a methyl or ethyl group. In one embodiment, the osmium complex may be as follows:

(Os organic molecule complex)-(Polymer)

One of the organic molecules which form the complex may optionally be attached to a polymer via a linker. Therefore, in another embodiment, the osmium complex may be as follows:

(Os organic molecule complex)-(Linker)-(Polymer)

Exemplary molecules are disclosed in the literature such as in Ohara, et al, Anal Chem. 1993 Dec. 1; 65(23):3512-7 and Antiochia et al, Materials Sciences and Applications Vol. 4 No. 7 A2(2013) (both incorporated by reference in their entirety). Examples of polymers containing an osmium complex include osmium bis(2,2'-bipyridine)chloride complexed poly(1-vinylimidazole), osmium bis(2,2'-bipyridine) chloride complexed poly(4-vinylpiridine), poly(1-vinylimidazole)$_n$-[osmium(4,4'-dimethyl-2,2'-bipyridyl)$_2$Cl$^2$]$^{2+/+}$, and derivatives thereof.

The solution may be deposited on a carbon sensor to form an active electrode area serving as the working electrode comprising redox polymer-wired GDH. A mixture of membrane polymer and cross-linker solutions can be added to form a membrane on the sensor. The membrane may comprise a polymer such as poly(1-vinylimidazole), poly(4-vinylpyridine), derivatives or combinations thereof. The polymers containing the osmium complex above may be used in combination with such membrane polymers to form a hydrogel film.

In one embodiment, the glucose sensor may comprise a printed electrode. In such case, an electrode may be formed on an insulated substrate. Specifically, an electrode may be formed on a substrate by means of photolithography or printing techniques, such as screen printing, gravure printing, or flexography. Examples of materials constituting insulated substrates include silicon, glass, ceramics, polyvinyl chloride, polyethylene, polypropylene, and polyester. Materials exhibiting high tolerance against various solvents or chemicals may be used.

In one embodiment, the FAD-GDH electrode or the glucose sensor may comprise ionic polymer, for example, polyethyleneimine (PEI), polyacrylic acid (PA), ε-polylysine, α-polylysine or polystyrene. The molecular weight of these polymers are not limited and any type may be used.

Glucose measurement may be carried out as follows. A buffer is placed in a thermostatic cell and maintained at a certain temperature. Potassium ferricyanide or phenazine methosulfate can be used as the mediator. A working electrode comprising immobilized FAD-GDH, a counter electrode (such as a platinum electrode) and a reference electrode (such as an Ag/AgCl electrode) are prepared. A constant voltage is applied to the carbon electrode, and after the current is stable, a sample containing glucose is added followed by measurement of the increase in current. The glucose concentration in the sample can then be computed against a calibration curve prepared with glucose concentrations having known standard concentrations.

In one example, 1.5 U of FAD-GDH is immobilized on a glassy carbon (GC) electrode and the response current value with respect to glucose concentration is measured. 1.8 ml of 50 mM potassium phosphate buffer (pH 6.0) and 0.2 ml of a 1 M aqueous solution of potassium hexacyanoferrate (III) (potassium ferricyanide) are added to the electrolysis cell. The GC electrode is connected to a BAS100B/W potentiostat (BAS Co., Ltd.) and the solution is stirred at 37° C. followed by applying a voltage of +500 mV to the Ag/AgCl reference electrode. In another example, the voltage applied to the Ag/AgCl reference electrode may be selected from, but not limited to, a voltage between −100 to +550, e.g., +400 mV. Glucose solutions having final concentrations of, e.g., 1 mM, 2 mM, 3 mM, 4 mM, 5 mM, 10 mM, 20 mM, 30 mM and 40 mM are added to these systems followed by measurement of the steady-state current value for each addition. These current values are plotted against known glucose concentrations (e.g., 1 mM, 2 mM, 3 mM, 4 mM 5 mM, 10 mM, 20 mM, 30 mM and 40 mM) to prepare a calibration curve. Glucose concentration can be quantified by comparing measured values against the calibration curve.

In another example, cyclic voltammetry can be carried out with the immobilized FAD-GDH described herein and conventional means. Measurements can be made by sweeping from 0 to +600 mV. Then, a certain voltage can be selected to measure the glucose concentration of a sample. This can be done by preparing a calibration curve as described above and then measuring the response current of the sample with unknown glucose concentration.

In one embodiment, the glucose sensor comprising FAD-GDH or the working electrode comprising the FAD-GDH may comprise a protective film (protective membrane).

The enzyme activity of a GOD may be determined using the same assay system as that for evaluating GDH activity, such as an assay system in which an excessive amount of mediator is present to accept the electron. Alternatively, the enzyme activity of a GOD may be determined using an assay system in which oxygen is the acceptor. Alternatively, the enzyme activity of a GOD may be determined following instructions of the manufacturer. The enzyme activity should be measured using the same system for initial activity and for residual activity in order to compute the residual activity ratio.

The following is an exemplary assay method for measuring GOD activity. Other methods may be employed as well.

GOD Assay Principle:

beta-D-Glucose+$O_2$+$H_2O$→D-Glucono-delta-lactone+$H_2O_2$ (catalyzed by GOD)

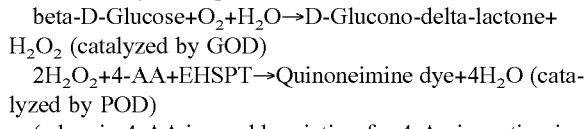

(wherein 4-AA is an abbreviation for 4-Aminoantipyrine and EHSPT is an abbreviation for N-Ethyl-N-(2-hydroxy-3-sulfopropyl)-m-toluidine)

Production of quinoneimine can be measured spectrophotometrically.

Definition of a Unit:

A GOD unit may be defined as enzyme activity capable of causing formation of one micromole of hydrogen peroxide (½ micromole of quinoneimine dye) per minute under the following conditions.

GOD Assay Method:

Reagents A-F are as follows

A. MES-Na buffer pH 5.7: 0.1M (Dissolve 2.13 g of 2-(N-morpholino) ethansulfonic acid (MW=213.25) in ca. 60 ml $H_2O$, adjust the pH to 5.7 with 1N NaOH at 25° C., fill up to 100 ml with $H_2O$)

B. Glucose solution: 15% (Dissolve 1.5 g of β-D-glucose and fill up to 10 ml with $H_2O$) (should be prepared fresh)

C. 4-AA solution: 0.5% (50 mg of 4-aminoantipyrine (MW=203.25)/10 ml of $H_2O$)

D. EHSPT solution: 40 mM (118 mg of N-Ethyl-N-(2-hydroxy-3-sulfopropyl)-m-toluidine (MW=295.3)/10 ml of $H_2O$)

E. Peroxidase solution: 500 U (expressed in terms of purpurogalin unit)/ml in $H_2O$ F. Enzyme diluent: 10 mM MES-Na buffer, pH 5.7, comprising 0.1% Triton X-100

Concentration in the assay mixture:

MES buffer: 79 mM

D-Glucose: 131 mM

4-AA: 0.2 mM

EHSPT: 0.3 mM

POD: ca.4 U/ml

Procedure:

Step 1. Prepare the following working solution freshly in a brownish bottle and store on ice.
30 ml Buffer solution (A)
6 ml Substrate solution (B)
0.3 ml 4-AA solution (C)
0.3 ml EHSPT solution (D)
0.3 ml POD solution (E)

Step 2. Pipette 3.0 ml of working solution into a cuvette (d=1.0 cm) and equilibrate at 37° C. for about 5 minutes.

Step 3. Add 0.1 ml of the enzyme solution* and mix gently with inversion. (* Dissolve the enzyme preparation in ice cold enzyme diluent (F) and dilute to 0.05-0.2 U/ml with the same buffer, immediately before the assay.)

Step 4. Record the increase in optical density at 555 nm against water for 2-3 min in a spectrophotometer thermostated at 37° C., and calculate the Δ OD per minute from the initial linear portion of the curve (Δ OD test).

In addition, measure the blank rate (Δ OD blank) by using the same method as the test with the proviso that enzyme diluent (F) is added instead of the enzyme solution.

GOD Activity can be calculated as follows:

$$\Delta OD/min\ (\Delta OD\ test - \Delta OD\ blank) \times Vt \times df$$

Volume activity (U/ml) =

$$\frac{\Delta OD/min\ (\Delta OD\ test - \Delta OD\ blank) \times Vt \times df}{32.8 \times 1/2 \times 1.0 \times Vs} = \Delta OD \times 1.89 \times df$$

Weight activity (U/mg)=(U/ml)×1/C
Vt: Total volume (3.1 ml)
Vs: Sample volume (0.1 ml)
32.8: Millimolar extinction coefficient of quinoneimine dye under the assay conditions ($cm^2$/micromole)
½: Factor based on the fact that 1 mole of $H_2O_2$ produces a half of one mole of quinoneimine dye.
1.0: Light path length (cm)
df: Dilution factor
C: Enzyme concentration in dissolution (c mg/ml).

The following examples describe aspects of the present invention in detail. However, the technical scope of the present invention is not to be construed or limited in any way to the following examples. Optional features, modification and variation of the concepts herein disclosed may be resorted to by those skilled in the art, and such modifications and variations are considered within the scope of this technology.

Example 1

Unless indicated otherwise, the assessment of heat stability and storage stability of GDH and GOD were carried out according to the test method below.

Test Method (1) Introduction of the GDH gene from a microorganism belonging to the genus *Mucor* and confirmation of GDH activity in the transformant Briefly, a GDH from a microorganism belonging to the genus *Mucor* (MpGDH, SEQ ID NO:1) was modified by introducing mutations N66Y/N68G/C88A/Q233R/T387C/E554D/L557V/S559K thereto to obtain a gene encoding a modified GDH (which may be referred to herein as MpGDH-M1, or GDH-M1). The amino acid sequence of MpGDH-M1 is indicated in SEQ ID NO: 3, while the base sequence is indicated in SEQ ID NO: 4. A DNA construct was obtained by introducing the MpGDH-M1 gene into the multi-cloning site of plasmid pUC19. More specifically, the pUC19 linearized Vector in the In-Fusion HD Cloning Kit (Clontech) was used as the pUC19 vector. The MpGDH-M1 gene was connected to the In-Fusion Cloning Site of the multi-cloning site of pUC19 by using said In-Fusion HD Cloning Kit according to the protocol in the instructions of the kit to obtain the construct plasmid (pUC19-MpGDH-M1).

The obtained recombinant plasmid pUC19-MpGDH-M1 was used as the template and PCR reaction using synthesized oligonucleotides of SEQ ID NOs: 5 to 10 and KOD-Plus-(Toyobo) was carried out with the following conditions. 5 μl of 10×KOD-Plus-buffer, 5 μl of a mixture solution comprising 2 mM of each dNTP, 2 μl of 25 mM MgSO4 solution, 50 ng of the DNA construct comprising the connected template MpGDH-M1 gene, 15 pmol of each of the synthesized oligonucleotides above, and 1 Unit of KOD-Plus- were added and the total volume was adjusted to 50 μl with sterile water. The prepared reaction solution was applied to a thermal cycler (Eppendorf) and incubated at 94° C. for 2 min, and then the cycle "94° C. for 15 seconds"-"50° C. for 30 seconds"-"68° C. for 8 minutes" was repeated 30 times. A portion of the reaction solution was applied to 1.0% agarose gel and electrophoresis was carried out and it was confirmed that the DNA fragment of about 8,000 bp was specifically amplified. The obtained DNA was digested with the restriction enzyme DpnI (NEW ENGLAND BIOLABS) and after cleaving the remaining template DNA, *E. coli*. strain JM 109 was transformed and spread out on LB-amp agar medium. Colonies which grew were inoculated to 2.5 mL of LB-amp medium (containing 1% (W/V) bactotryptone, 0.5% (W/V) peptone, 0.5% (W/V) NaCl, 50 μg/ml Ampicillin) and shake cultured at 37° C. for 20 hours to obtain the culture. Bacterial cells were obtained by carrying out centrifugation 7,000 rpm for 5 minutes to collect the cells. Then the bacterial cells were applied to recombinant plasmid extraction using QIAGEN tip-100 (QIAGEN) to extract and purify the recombinant plasmid and 2.5 μg DNA was obtained. The DNA base sequence encoding MpGDH-M1 in said plasmid was determined using the multi-capillary DNA analysis system Applied Biosystems 3130xl Genetic Analyzer (Life Technologies) and, as a result, a DNA construct (SEQ ID NO:11) encoding the mutant MpGDH-M1/A175C/N214C/G466D (SEQ ID NO:12) was obtained (also referred to herein as MpGDH-M2, or GDH-M2). This gene was expressed in *Aspergillus sojae* and the GDH activity thereof was confirmed.

More specifically, a GDH gene from a microorganism belonging to the genus *Mucor* was used as the starting material and a modified GDH gene was designed to obtain a GDH suitable for recombinant expression in *Aspergillus sojae*. More specifically, based on the GDH gene sequence of SEQ ID NO:1, a codon optimized gene sequence with codon frequency adapted for expression in the host was designed and the entire gene was synthesized. This wholly synthesized DNA sequence is indicated in SEQ ID NO:2.

Double-joint PCR (Fungal Genetics and Biology, 2004, volume no. 41, pp. 973-981) was carried out to construct a cassette consisting of 5' arm region—PyrG gene (uracil auxotrophy marker)—TEF1 promotor gene—flavin binding GDH gene-3' arm region. This cassette was to transform of a pyrG deficient strain from *Aspergillus sojae* strain NBRC4239 (a strain in which 48 base pairs upstream, the 896 bp coding region and downstream 240 base pairs of the pyrG gene is deleted) as follows. Conidia of the pyrG-disrupted strain from *Aspergillus sojae* NBRC 4239 was inoculated to 100 ml of polypeptone dextrin liquid medium comprising 20 mM uridine in a 500 ml Erlenmeyer flask and after shaking the culture at 30° C. for about 20 hours, the cells were recovered. Protoplasts were prepared from the recovered cells. Transformation was carried out by using the protoplast PEG method with the obtained protoplasts and 20 µg of the target gene-inserted DNA construct. Subsequently, the cells were incubated at 30° C. for 5 days or more with Czapek-Dox minimal medium (Difco Co., pH 6) containing 0.5% (w/v) agar and 1.2 M sorbitol to obtain transformed *Aspergillus sojae* having the capability to form colonies.

In the resulting transformed *Aspergillus sojae*, pyrG, which is a gene capable of complementing uridine auxotrophy, is introduced and, therefore, the transformants can grow on uridine-free medium and can be selected as those strains in which the gene of interest was introduced. From the obtained strains, the desired transformants were selected by confirmation with PCR. *Aspergillus sojae* transformed with the MpGDH-M2 gene was used and GDH was produced.

Conidia of each strain were inoculated to 40 mL of DPY liquid medium (1% (w/v) polypeptone, 2% (w/v) dextrin, 0.5% (w/v) yeast extract, 0.5% (w/v) $KH_2PO_4$, 0.05% (w/v) $MgSO_4.7H_2O$; pH not adjusted) in a 200 ml Erlenmeyer flask and shaking culture was performed at 30° C. for 4 days at 160 rpm. Next, the cells were filtered from the culture after cultivation, and the supernatant fraction of the resulting medium was concentrated to 10 mL with Amicon Ultra-15, 30 K NMWL (Millipore). Then, this was applied to a HiLoad 26/60 Superdex 200 pg (GE Healthcare) column equilibrated with 20 mM potassium phosphate buffer (pH 6.5) containing 150 mM NaCl and eluted with the same buffer. Fractions exhibiting GDH activity were collected to obtain the purified product of MpGDH-M2.

(2) Heat stability evaluation of GDH and GOD

A GOD from *Aspergillus niger* was purchase from Sigma-Aldrich (Type X-S, referred to herein as GOD-1). Another GOD from *Aspergillus* sp. was purchase from Toyobo (Catalog No. GLO-201, referred to herein as GOD-2). A GOD from *Aspergillus niger* was purchase from Wako Pure Chemical Industries, Ltd (Catalog No. 074-02401, referred to herein as GOD-3). Another GOD from *Aspergillus niger* was purchase from Sigma-Aldrich (Type VII, referred to herein as GOD-4). The GDH designated as GLD3 was purchased from Funakoshi (the amino terminus of this enzyme was found to be identical to that of the GDH from *Mucor hiemalis* and it is highly plausible that this enzyme is from *Mucor hiemalis*, a microorganism belonging to the genus *Mucor*) (GLD3 may also be referred to herein as GDH-GLD3). When using GLD3, ultrafiltration was carried out using Amicon ultra 0.5 ml filter (Merck, cutoff 30 kDa) to remove low molecular weight constituents, and the solution was replaced with PBS (pH 7.4). MpGDH-M2 was prepared as above. The enzyme is diluted to retrieve a diluted enzyme solution of about 1 U/ml (100 mM potassium phosphate buffer, pH 7.0). A pair of such enzyme solutions each having 0.1 mL are prepared and one is preserved at 4° C. while the other is subjected to heat treatment for 15 minutes at 57° C., pH 7.

After heat treatment, the activity of each enzyme is determined and the "residual activity ration (%)" is computed as the percentage of residual activity after heat treatment for 15 minutes at 57° C., pH 7(%) compared to the enzyme activity of the enzyme preserved at 4° C. (100%). Results are shown in FIG. 1. GODs exhibited superior heat stability and were stable under harsh temperature conditions compared to GDHs.

(3) Storage Stability Evaluation of GDH and GOD

Figure 2:
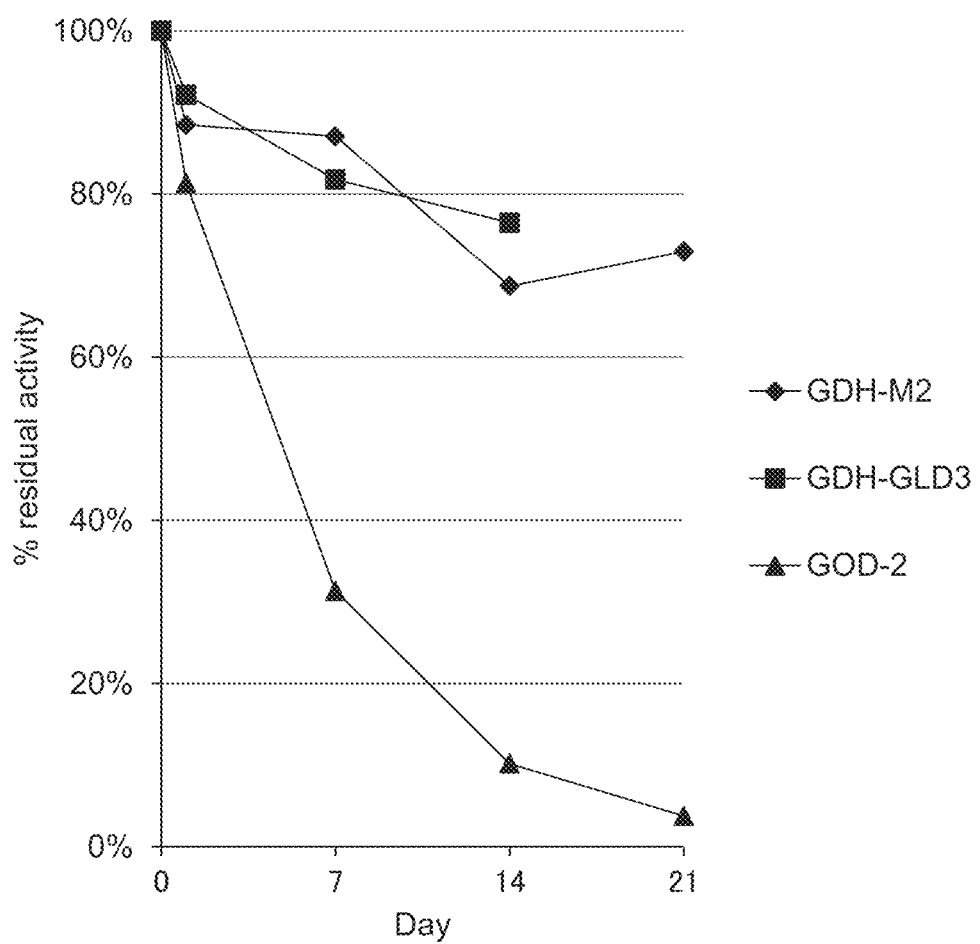
FIG. 2 shows residual enzyme activity of different types of GDH and GOD after maintaining at 40° C. for up to 21 days.
Figure 3:
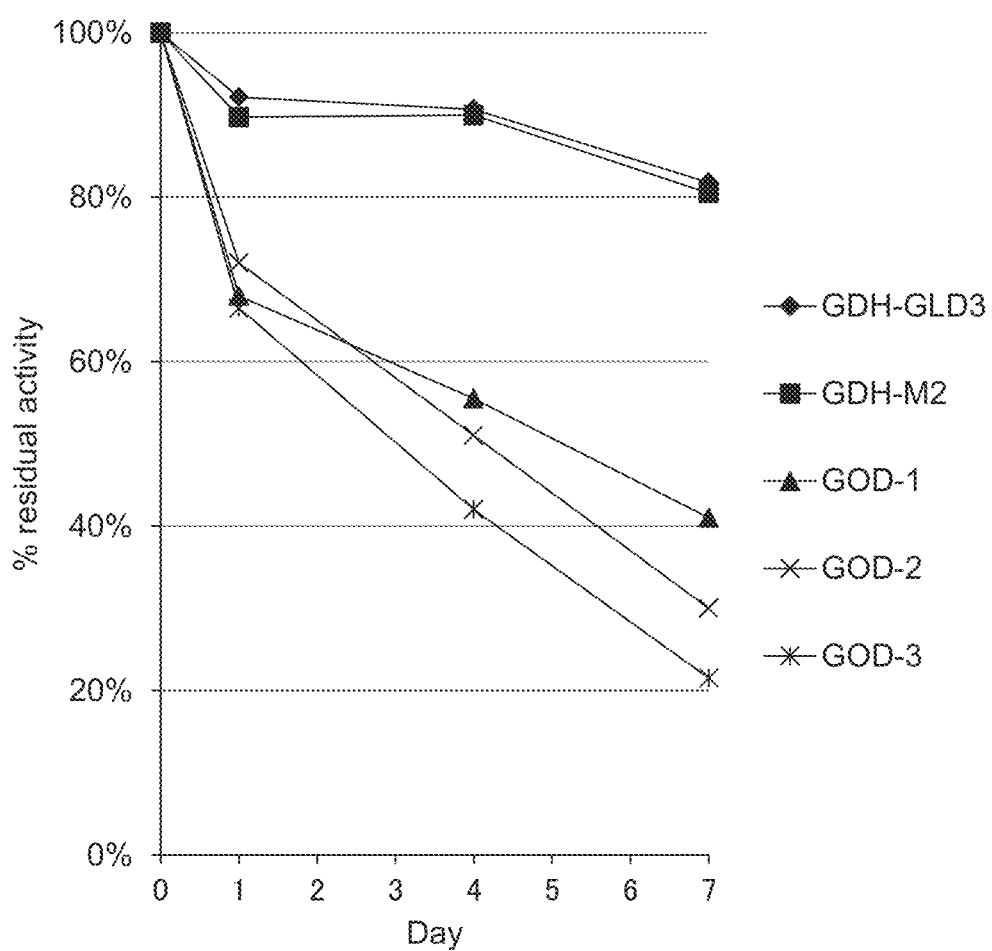
FIG. 3 shows residual enzyme activity of different types of GDHs and GODs after maintaining at 40° C. for up to 7 days.
Figure 4:
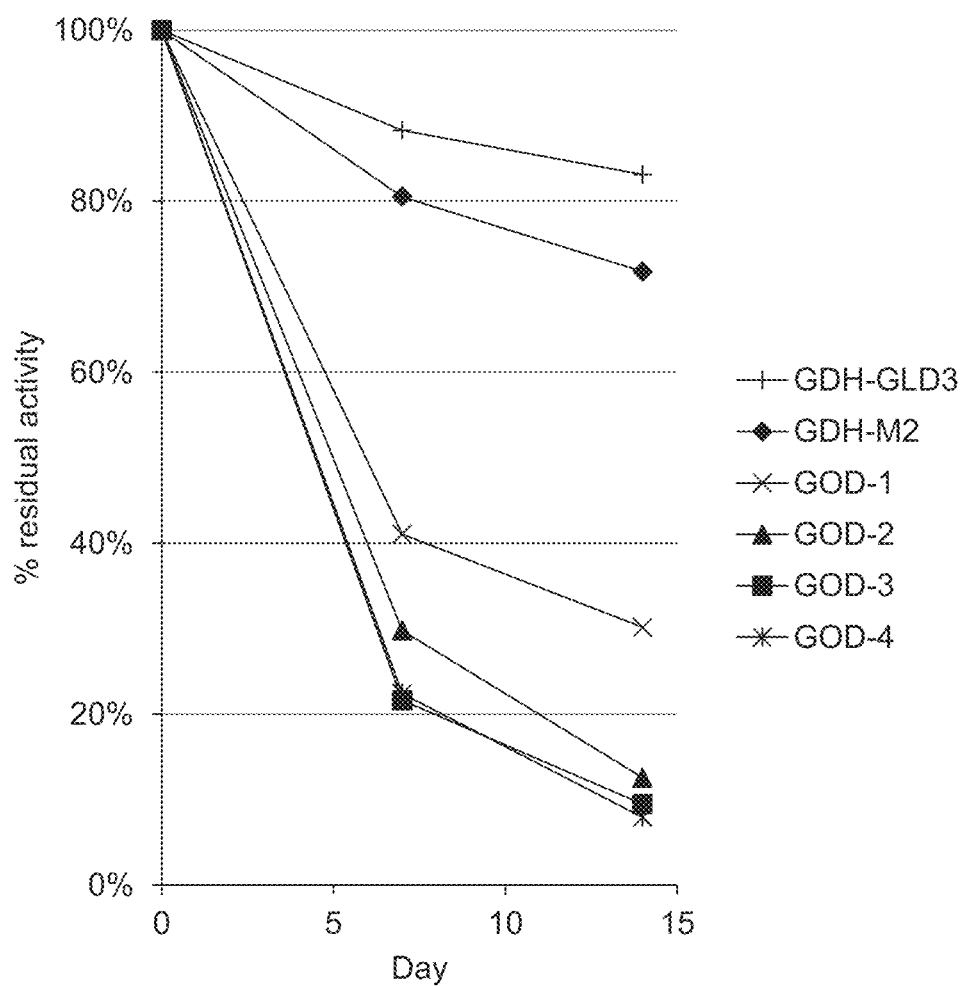
FIG. 4 shows residual enzyme activity of different types of GDHs after maintaining at 40° C. for up to 14 days.

The solutions of 1 mg/ml of each GDH and GOD were replaced with PBS solution and stored at 40° C. for a prolonged period of time. After a day, 4 days, 1 week, 2 weeks and 3 weeks, the GDH activity or GOD activity of each enzyme was measured. The "remaining activity rate (%)" was computed as the activity value after storage at 40° (%) C. by setting the activity value before storage at 40° C. as 100%. Results are shown in FIGS. 2 to 4.

As a result, after 1 week, the residual activity ratio of GOD-3 was 22%, GOD-4 was 22%, GOD-2 was 30%, and GOD-1 was 41%. That is, after 1 week at 40° C., all GODs exhibited a significant decrease in activity. Further, after 2 weeks, the residual activity ratio of GOD-3 was 9%, GOD-4 was 8%, GOD-2 was 13%, and GOD-1 was 30% and again all GODs exhibited a significant decrease in activity.

On the other hand, after one week, the residual activity ratio of MpGDH-M2 was 80%, and that of GLD3 was 88%. That is, GDHs retained their activity over a prolonged period of time. After 2 weeks, the residual activity ratio of MpGDH-M2 after was 72%, and that of GLD3 was 83% and again the GDHs retained their activity over a prolonged period of time. Even after 3 weeks, MpGDH-M2 retained about 73% of its initial activity, whereas GOD-2 lost most of its activity over the same period of time (4%). See FIG. 2.

When comparing the residual activity after treatment at 57° C., pH 7 for 15 minutes, each GOD had both higher residual activity and higher stability than MpGDH-M2 and GLD3. However, it was found that, surprisingly, the stability of GODs were lower in the 40° C. storage test compared to said GDHs, and it was found that GODs, despite their superior heat stability under harsh temperature conditions, may not be optimal for use in CGM. Rather, GDHs proved to be suited for long term use such as in CGM.

Since the GDHs retained relatively high activity even in the 40° C. storage test, it is highly plausible that said GDHs will also retain relatively high activity when stored at 37° C.

Example 2

Storage stability test of GDH/GOD immobilized electrodes

GDH/GOD immobilized electrodes were produced and tested for storage stability as follows.

Method of Producing the Electrode

3 µl of 5% polyethyleneimine (PEI) (catalogue no. 164-17821, average molecular weight 10000, from Wako), which is a cationic polymer, is added onto a screen printed electrode based on carbon and then dried. Next, 0.5 µl of osmium polymer (catalogue no. 002096, BAS) treated at 98° C. for 1 hour is added and then dried. Next, 3 µl of 35 mg/ml GDH/GOD is added and then dried. Next, 3 µl of 2% polyethylene glycol diglycidyl ether (PEGDE, average molecular weight 500, manufactured by Sigma-Aldrich) is added and stored at 4° C. overnight.

Electrodes were also produced using 1% polyacrylic acid (PA) (catalogue no. 416037-100 ML, average molecular weight 15000, from Sigma-Aldrich), which is an anionic polymer, instead of PEI.

Storage Stability Test

The electrodes produced as above were washed with ultrapure water and dried at 30° C. for 1 hour. Next, for every 2 hours, the electrodes were taken and subjected to electrochemical measurement. After the electrochemical measurement, the electrode was again stored in an incubator at 30° C. in a dry state.

Electrochemical Measurement

The reference electrode Ag/AgCl, the counter electrode (platinum) and the screen printed electrode based on GDH or GOD as the working electrode were placed in 100 mM potassium phosphate buffer (pH 7). Then, cyclic voltammetry measurement sweeping from 0 to +600 mV was carried out.

The oxidation current values at +500 mV for a condition where no glucose was added and a condition where 5 mM glucose was added were compared and the difference was taken as the response current value. Measurements were carried out at 0, 2 and 4 hrs, and the relative value was recorded taking the response current value at 0 hr as 100%.

Results

Figure 5:
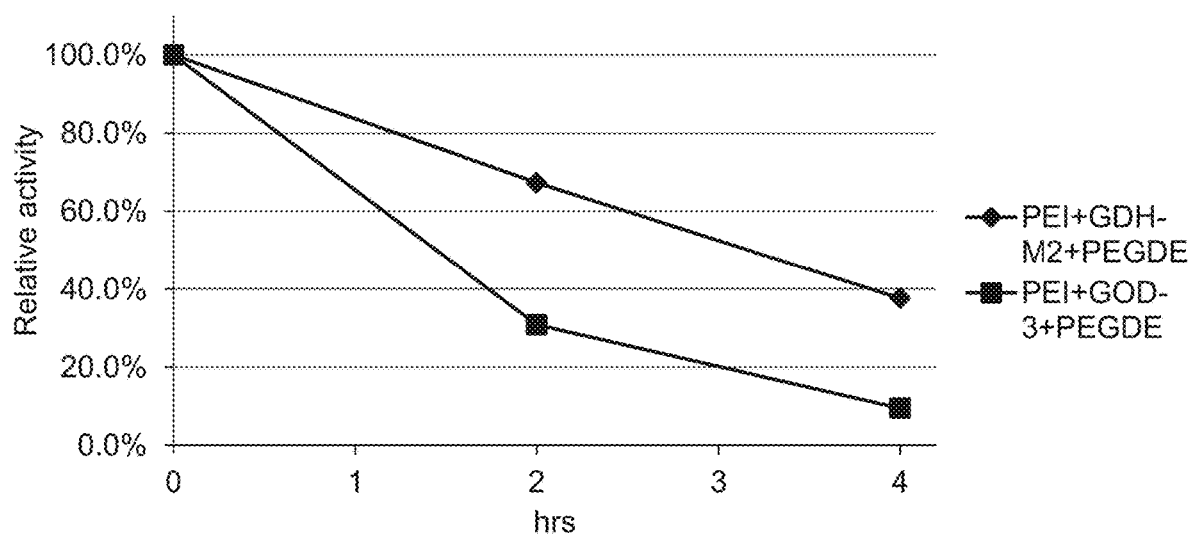
FIG. 5 shows residual enzyme activity at 0 to 4 hours for GDH-M2 or GOD-3 immobilized electrode using PEI and PEGDE.

For the electrodes produced by using PEI, the response current of the GDH-M2 electrode was 67.3% after for 2 hours. By comparison, GOD-3 lost much activity and the residual response current of the GOD-3 electrode was a mere 30.8% at 2 hours. Similar results were observed after 4 hours of storage and the relative response current value of GOD-3 was lower than that of GDH-M2. See FIG. 5.

Figure 6:
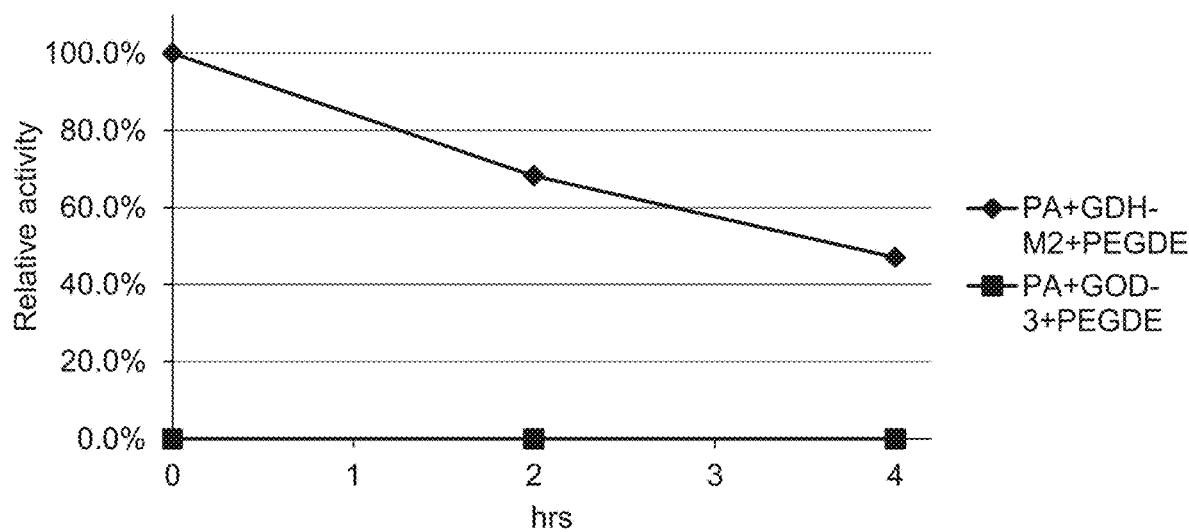
FIG. 6 shows residual enzyme activity at 0 to 4 hours for GDH-M2 or GOD-3 immobilized electrodes using PA and PEGDE.

For the electrodes produced by using PA, no response current could be observed with the GOD-3 immobilized electrode even at 0 hours. By contrast, the response current could be observed for the GDH-M2 immobilized electrode using PA. After 2 hours of storage, 68.3% of activity was retained, and after 4 hours, 47.1% of initial activity was retrained, showing stability superior to the electrode immobilized by using PEI. See FIG. 6.

It should be noted that the electrodes evaluated in this experiment have no protective film and thus the conditions are more harsh and severe than conditions in actual CGM. Sensors with glucose dehydrogenases which exhibit higher storage stability than sensors with glucose oxidases, which are used in current CGM devices, can be used advantageously for measurements over long periods.

Example 3

Optimal pH

The optimal pH of the glucose dehydrogenases GDH-M2 and GLD3 were evaluated.

Figure 7:
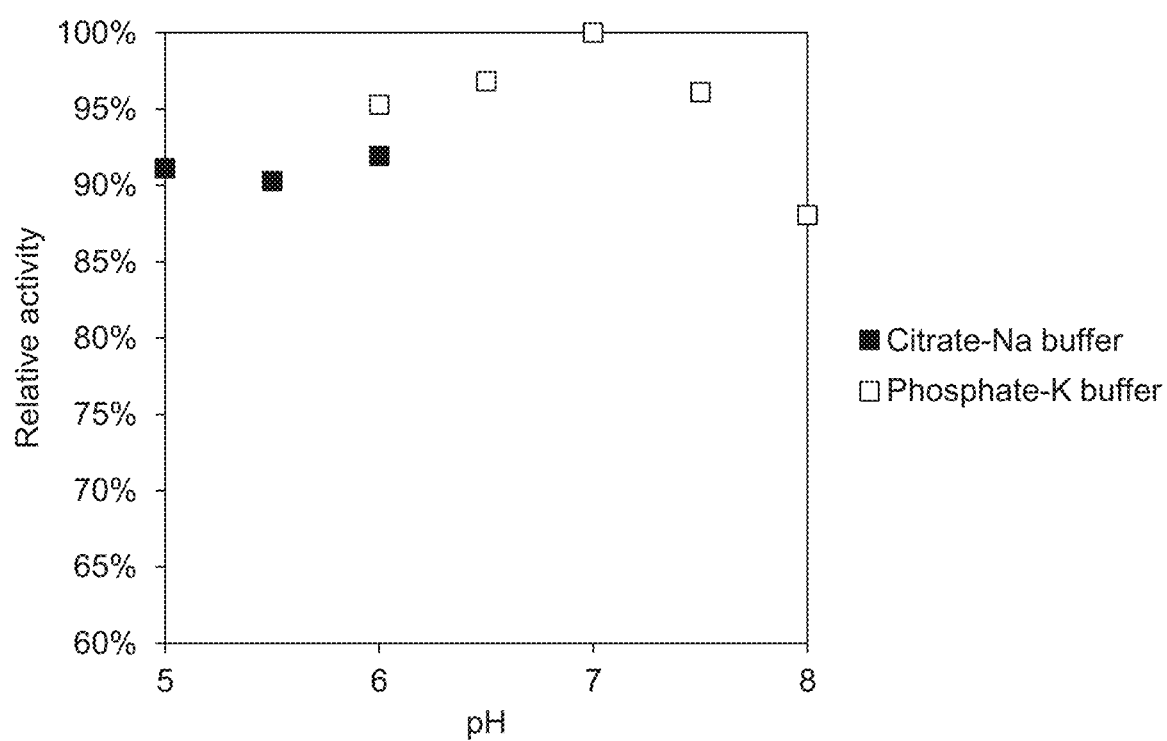
FIG. 7 shows optimal pH of GDH-M2.
Figure 8:
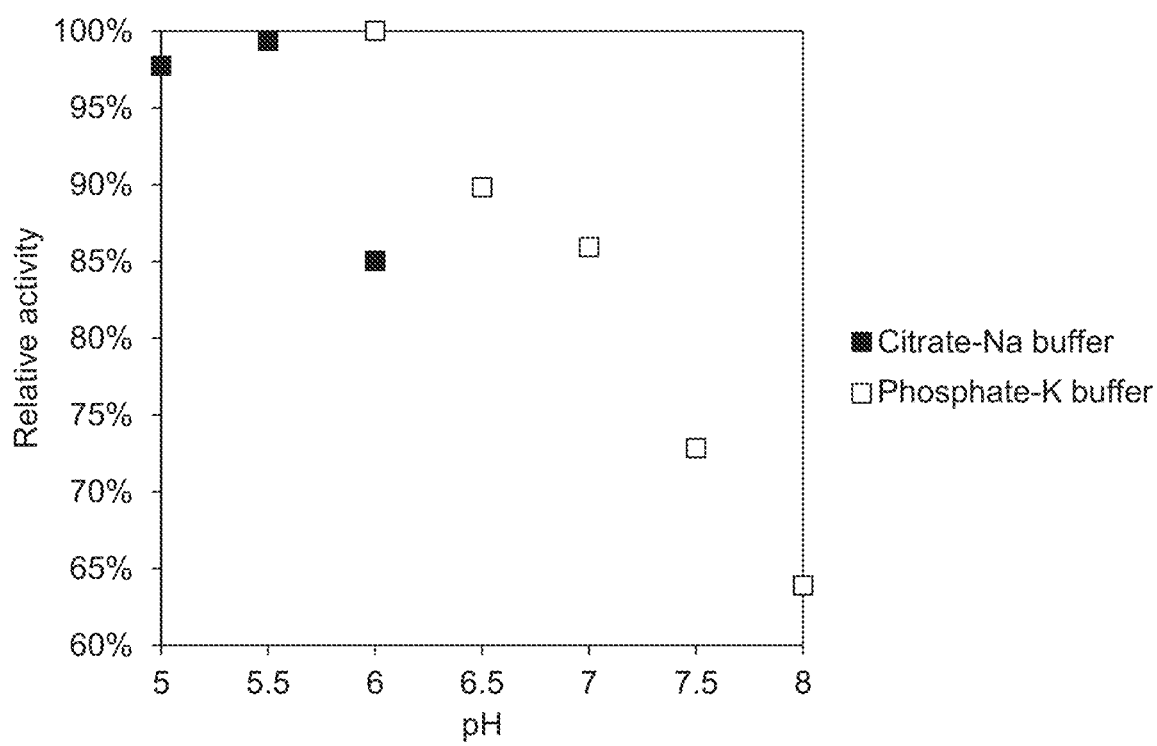
FIG. 8 shows optimal pH of GLD3.

Activity assay was carried out as follows. The 2,6-dichloro-indophenol (DCIP) assay was performed by measuring the time-dependent reduction of DCIP at 520 nm (300 mM DCIP/1 mM PMS/400 mM Glucose). Citrate-sodium buffer was used for pH 5.5 to 6.0 while phosphate-potassium buffer was used for pH 6 to 8. See FIG. 7 (GDH-M2) and FIG. 8 (GLD3).

By way of comparison, the optimal pH of GOD-3 is reported to be pH 5.6 according to the manufactures' catalogue.

Example 4

Glucose Concentration Dependency

The glucose concentration dependency of the electrodes with immobilized enzymes was evaluated as follows.

The sensors was prepared using PEI, GDH-M2, an Os polymer, and PEGDE as in Example 2 above. Next, the electrode was placed in 10 ml of 100 mM potassium phosphate buffer solution (pH 7) together with an Ag/AgCl reference electrode and Platinum counter electrode (auxiliary electrode) to compose a three-electrode system. The measurements were carried out with this three-electrode system.

Figure 9:
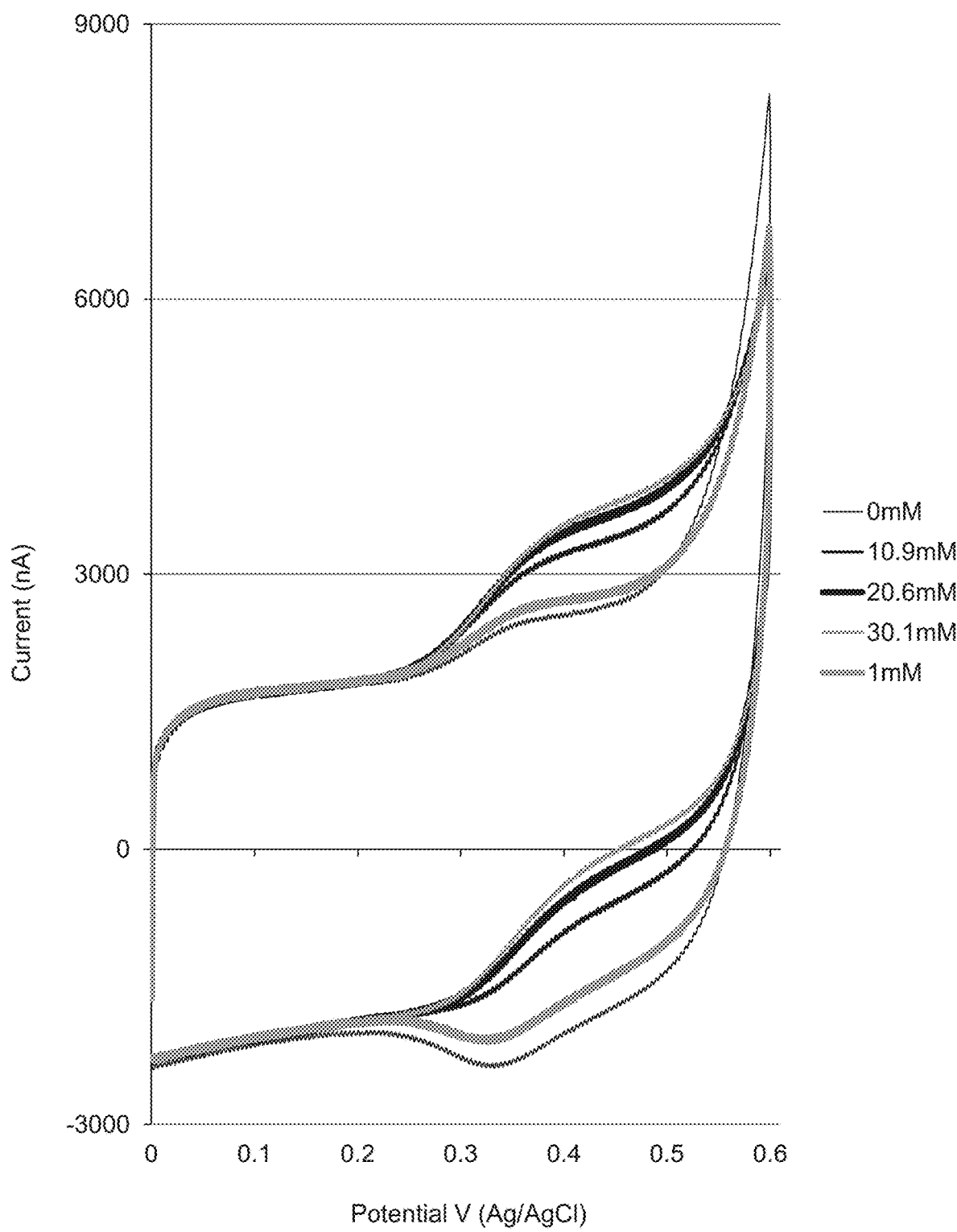
FIG. 9 shows a cyclic voltammetry using the GDH-M2 electrode.
Figure 10:
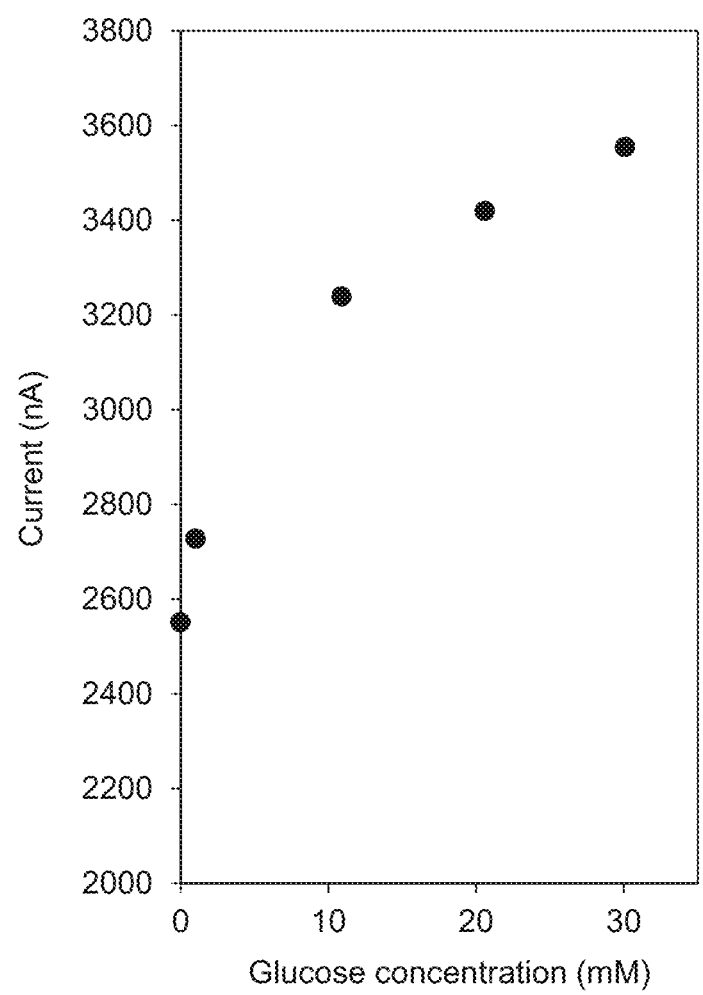
FIG. 10 shows glucose concentration dependency of the response current. Oxidation current value was recorded at 0.4V.

While stirring at 350 rpm, a predetermined concentration of glucose was added. Then, cyclic voltammetry measurement sweeping from 0 to +600 mV was carried out and the oxidation current value at +400 mV was recorded. Results are shown in FIGS. 9 and 10.

It was demonstrated that glucose concentration dependency of the response current could be confirmed from 1 to 30.1 mM glucose.

Example 5

Molecular Weight

Figure 11:
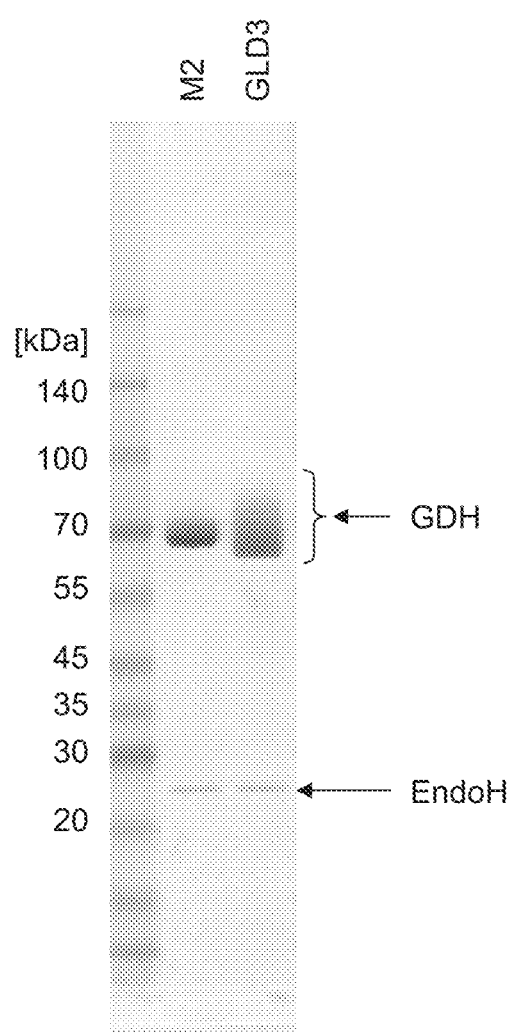
FIG. 11 shows SDS-PAGE of GDH-M2 and GLD3.

The molecular weights of the enzymes were evaluated with SDS-PAGE as follows. EndoH endoglycosidase (New England Biolabs) treatment was carried out at 37° C. for 24 hours. Then SDS-PAGE was carried out with a 5-20% gradient gel. The molecular weight of M2 was about 70 kDa and that of GLD3 was about 65 to 80 kDa. See FIG. 11.

Example 6

Substrate Specificity

The substrate specificity of GDH-M2 was evaluated as follows. More specifically, the concentration of the substrate sugar was 200 mM. Activity on glucose was set as 100% and relative activity on other substrates is expressed in terms of percentage.

TABLE 1

|  | GDH-M2 | GLD3 |
| --- | --- | --- |
| Glucose | 100% | 100% |
| Maltose | 0.37% | 0.67% |
| Xylose | 0.55% | 1.60% |

*Values of GLD3 are those according to the catalog provided by the manufacturer.

Each patent, patent application, publication and document referenced herein hereby is incorporated by reference in its entirety. Citation or reference of the above patents, patent applications, publications and documents is not an admission that any of the foregoing is pertinent prior art, nor does it constitute any admission as to the contents or date of these publications or documents. Descriptions and definitions set forth in the present specification prevail over those in documents incorporated herein by reference. The technology illustratively described herein may suitably be practiced in absence of any element(s) not specifically disclosed herein. Terms and expressions which have been employed are used as terms of description and not of limitation. Use of such terms and expressions do not exclude any equivalents of the features shown and described or portions thereof, and various modifications are possible within the scope of the technology claimed. The term "a" or "an" can refer to one of or a plurality of the elements it modifies (e.g., "a reagent" can mean one or more reagents) unless the context clearly indicates either one of the elements or more than one of the elements is described. In each instance herein any of the terms "comprising," "consisting essentially of," and "consisting of" may be replaced with of the other two terms.

INDUSTRIAL APPLICABILITY

In some embodiments, the present methods can be used, e.g., for continuous glucose monitoring.

BRIEF DESCRIPTION OF SEQUENCES

SEQ ID NO: 1 *Mucor prainii* wt GDH aa
SEQ ID NO: 2 *Mucor prainii* wt GDH DNA
SEQ ID NO: 3 MpGDH-M1 aa
SEQ ID NO: 4 MpGDH-M1 DNA
SEQ ID NOs: 5-10 Primers
SEQ ID NO: 11 MpGDH-M2 aa
SEQ ID NO: 12 MpGDH-M2 DNA
SEQ ID NO: 13 MhGDH aa
SEQ ID NO: 14 MhGDH DNA

The invention claimed is:

1. A method of continuous glucose monitoring comprising using a glucose dehydrogenase (GDH) capable of
    (a) retaining 60% or more of the initial activity over a period of 1 week when retained at 40° C. in solution when retained at a pH of 7.4,
    (b) retaining 40% or more of the initial activity over a period of 2 weeks when retained at 40° C. in solution when retained at a pH of 7.4, or
    (c) retaining 30% or more of the initial activity over a period of 3 weeks when retained at 40° C. in solution when retained at a pH of 7.4,
    wherein said GDH is a flavin adenine dinucleotide (FAD) dependent GDH and wherein said GDH is neither a membrane bound protein nor GLD3,
    wherein the continuous glucose monitoring comprises
    i) bringing a sample containing glucose into contact with a glucose sensor, wherein the glucose sensor comprises an electrode, the GDH and a mediator, wherein the GDH is immobilized on the electrode and wherein the mediator is immobilized on the electrode,
    ii) applying a potential to the electrode, and
    iii) measuring the response current,
    wherein the continuous glucose monitoring is carried out for 1 day or more.

2. The method of claim 1, wherein continuous glucose monitoring can be carried out without re-calibration.

3. The method of claim 1, wherein the GDH has the following characteristics:
    (1) stability as defined in any one of (a) to (c) of claim 1,
    (2) substrate specificity: the reactivity to maltose is 2% or less, relative to the reactivity to D-glucose (100%);
    (3) optimal activity pH: 6.5 to 7.5; and
    (4) a molecular weight of about 65 to about 81 kDa when measured by sodium dodecyl sulfonate-polyacrylamide gel electrophoresis (SDS-PAGE).

4. The method of claim 1, wherein the continuous glucose monitoring is carried out over a period of 1 to 3 weeks.

* * * * *

SEQUENCE LISTING

<160> NUMBER OF SEQ ID NOS: 14

<210> SEQ ID NO 1
<211> LENGTH: 641
<212> TYPE: PRT
<213> ORGANISM: Mucor prainii

<400> SEQUENCE: 1

```
Met Lys Ile Thr Ala Ala Ile Ile Thr Val Ala Thr Ala Phe Ala Ser
1               5                   10                  15

Phe Ala Ser Ala Gln Gln Asp Thr Asn Ser Ser Thr Asp Thr Tyr
            20                  25                  30

Asp Tyr Val Ile Val Gly Gly Gly Val Ala Gly Leu Ala Leu Ala Ser
                35                  40                  45

Arg Ile Ser Glu Asn Lys Asp Val Thr Val Ala Val Leu Glu Ser Gly
        50                  55                  60

Pro Asn Ala Asn Asp Arg Phe Val Val Tyr Ala Pro Gly Met Tyr Gly
65                  70                  75                  80

Gln Ala Val Gly Thr Asp Leu Cys Pro Leu Ile Pro Thr Thr Pro Gln
                85                  90                  95

Glu Asn Met Gly Asn Arg Ser Leu Thr Ile Ala Thr Gly Arg Leu Leu
            100                 105                 110

Gly Gly Gly Ser Ala Ile Asn Gly Leu Val Trp Thr Arg Gly Gly Leu
        115                 120                 125

Lys Asp Tyr Asp Ala Trp Glu Glu Leu Gly Asn Pro Gly Trp Asn Gly
130                 135                 140

Ala Asn Leu Phe Lys Tyr Phe Lys Lys Val Glu Asn Phe Thr Pro Pro
145                 150                 155                 160

Thr Pro Ala Gln Ile Glu Tyr Gly Ala Thr Tyr Gln Lys Ser Ala His
                165                 170                 175

Gly Lys Lys Gly Pro Ile Asp Val Ser Phe Thr Asn Tyr Glu Phe Ser
            180                 185                 190

Gln Ser Ala Ser Trp Asn Ala Ser Leu Glu Thr Leu Asp Phe Thr Ala
        195                 200                 205

Leu Pro Asp Ile Leu Asn Gly Thr Leu Ala Gly Tyr Ser Thr Thr Pro
    210                 215                 220

Asn Ile Leu Asp Pro Glu Thr Val Gln Arg Val Asp Ser Tyr Thr Gly
225                 230                 235                 240

Tyr Ile Ala Pro Tyr Thr Ser Arg Asn Asn Leu Asn Val Leu Ala Asn
                245                 250                 255

His Thr Val Ser Arg Ile Gln Phe Ala Pro Lys Asn Gly Ser Glu Pro
            260                 265                 270

Leu Lys Ala Thr Gly Val Glu Trp Tyr Pro Thr Gly Asn Lys Asn Gln
        275                 280                 285

Lys Gln Ile Ile Lys Ala Arg Tyr Glu Val Ile Ile Ser Ser Gly Ala
    290                 295                 300

Ile Gly Ser Pro Lys Leu Leu Glu Ile Ser Gly Ile Gly Asn Lys Asp
305                 310                 315                 320

Ile Val Ser Ala Ala Gly Val Glu Ser Leu Ile Asp Leu Pro Gly Val
                325                 330                 335

Gly Ser Asn Met Gln Asp His Val His Ala Ile Thr Val Ser Thr Thr
            340                 345                 350

Asn Ile Thr Gly Tyr Thr Thr Asn Ser Val Phe Val Asn Glu Thr Leu
        355                 360                 365
```

| | | | | | | | | | | | |
|---|---|---|---|---|---|---|---|---|---|---|---|
|Ala|Gln|Glu|Gln|Arg|Glu|Glu|Tyr|Glu|Ala|Asn|Lys|Thr|Gly|Ile|Trp|
|370| | | | |375| | | | |380| | | | | |

Ala Thr Thr Pro Asn Asn Leu Gly Tyr Pro Thr Pro Glu Gln Leu Phe
385                 390                 395                 400

Asn Gly Thr Glu Phe Val Ser Gly Lys Glu Phe Ala Asp Lys Ile Arg
                405                 410                 415

Asn Ser Thr Asp Glu Trp Ala Asn Tyr Tyr Ala Ser Thr Asn Ala Ser
            420                 425                 430

Asn Val Glu Leu Leu Lys Lys Gln Tyr Ala Ile Val Ala Ser Arg Tyr
        435                 440                 445

Glu Glu Asn Tyr Leu Ser Pro Ile Glu Ile Asn Phe Thr Pro Gly Tyr
450                 455                 460

Glu Gly Ser Gly Asn Val Asp Leu Gln Asn Asn Lys Tyr Gln Thr Val
465                 470                 475                 480

Asn His Val Leu Ile Ala Pro Leu Ser Arg Gly Tyr Thr His Ile Asn
                485                 490                 495

Ser Ser Asp Val Glu Asp His Ser Val Ile Asn Pro Gln Tyr Tyr Ser
            500                 505                 510

His Pro Met Asp Ile Asp Val His Ile Ala Ser Thr Lys Leu Ala Arg
        515                 520                 525

Glu Ile Ile Thr Ala Ser Pro Gly Leu Gly Asp Ile Asn Ser Gly Glu
530                 535                 540

Ile Glu Pro Gly Met Asn Ile Thr Ser Glu Asp Asp Leu Arg Ser Trp
545                 550                 555                 560

Leu Ser Asn Asn Val Arg Ser Asp Trp His Pro Val Gly Thr Cys Ala
                565                 570                 575

Met Leu Pro Lys Glu Leu Gly Gly Val Val Ser Pro Ala Leu Met Val
            580                 585                 590

Tyr Gly Thr Ser Asn Leu Arg Val Val Asp Ala Ser Ile Met Pro Leu
        595                 600                 605

Glu Val Ser Ser His Leu Met Gln Pro Thr Tyr Gly Ile Ala Glu Lys
610                 615                 620

Ala Ala Asp Ile Ile Lys Asn Phe Tyr Lys Thr Gln His Lys Asn Gln
625                 630                 635                 640

Asn

<210> SEQ ID NO 2
<211> LENGTH: 1926
<212> TYPE: DNA
<213> ORGANISM: Mucor prainii

<400> SEQUENCE: 2

```
atgaagatca cagctgccat tatcactgtt gccacagcat ttgcttcttt tgcttctgct    60
caacaagaca caaattcttc ctcaactgat acttatgatt atgttatcgt tggcggcggt   120
gtagctggtt tggctttggc tagtcgtatc tctgaaaaca aggatgtcac tgttgctgtt   180
ctcgagtccg gtcctaatgc caatgataga tttgttgttt atgctcctgg catgtatggc   240
caagctgttg gcactgatct ctgtcctctc attcctacta ctcctcaaga aaatatgggc   300
aacagaagtc tcacaatcgc tactggtaga ttgctcggtg gtggcagtgc tattaatggt   360
ctcgtttgga cccgtggtgg cttgaaggat tacgatgctt gggaggagct cggtaaccct   420
ggatggaacg gtgccaactt gttcaagtac tttaagaagg tcgaaaactt cactcctcct   480
actcctgccc aaattgaata cggcgctact tatcagaaaa gtgctcatgg caagaaggga   540
```

```
cctattgatg tctctttcac gaactacgag ttctctcaat ctgctagctg gaacgcctca    600
ctcgaaaccc ttgatttcac tgcacttcct gatatcttga acggtacttt ggccggttac    660
tctaccactc ccaacatttt ggaccctgag actgttcaac gtgttgattc ctatactggt    720
tacattgctc cttacactag ccgtaacaac ctcaatgttt tggccaacca taccgtctcc    780
cgcattcaat ttgctcccaa gaatggtagc gaacctctca aggctaccgg tgttgaatgg    840
tatcccactg gcaacaagaa tcaaaagcaa attatcaagg cccgttatga agttatcatc    900
tcatctggtg ccattggtag tcctaagctt ttggaaatct ctggtatcgg taataaggat    960
atcgtctctg ctgctggtgt cgagtccttg attgacttgc ctggcgttgg ttccaacatg   1020
caagatcacg ttcatgctat cactgtctct actaccaata ttactggcta tactaccaac   1080
agcgtctttg tcaatgaaac ccttgcccaa gaacaaagag aagaatatga agccaacaag   1140
actggtatct gggctactac tcccaacaac ctcggttatc ctacgcccga caactcttc    1200 aatggcaccg aattcgtttc tggaaaggag tttgctgaca agattcgtaa ctctactgat   1260
gaatgggcca actattatgc ttccaccaac gcctccaatg tcgagttatt aaagaagcaa   1320
tatgctattg tcgcctctcg ttacgaagag aactacttgt ctcctattga aatcaacttc   1380
actcctggtt atgagggtag cggtaatgtc gatttgcaaa acaacaagta ccaaactgtc   1440
aaccatgtct tgattgctcc tttaagtcgt ggttatactc acattaactc ttctgatgtg   1500
gaggatcatt ctgtcattaa tccccaatac tactctcatc tatggatat tgatgtccat    1560 atcgcttcca ctaaacttgc tcgcgaaatc atcactgcct ctcccggtct tggtgacatt   1620
aacagtggcg aaatcgaacc cggtatgaat attacttctg aagacgacct tagatcttgg   1680
ttgagtaata atgtccgttc tgactggcat cctgttggta cttgtgctat gcttcccaag   1740
gaattaggtg tgttgtcag ccccgctctc atggtttacg gcacttccaa cttgcgtgtt    1800
gttgatgctt cgattatgcc cctcgaagtc tcttctcatt tgatgcaacc cacctacggt   1860
attgctgaga aggctgctga cattattaag aatttctaca agactcaaca caagaaccaa   1920
aattag                                                              1926

<210> SEQ ID NO 3
<211> LENGTH: 641
<212> TYPE: PRT
<213> ORGANISM: Mucor prainii

<400> SEQUENCE: 3

Met Lys Ile Thr Ala Ala Ile Ile Thr Val Ala Thr Ala Phe Ala Ser
1               5                   10                  15

Phe Ala Ser Ala Gln Gln Asp Thr Asn Ser Ser Thr Asp Thr Tyr
            20                  25                  30

Asp Tyr Val Ile Val Gly Gly Gly Val Ala Gly Leu Ala Leu Ala Ser
        35                  40                  45

Arg Ile Ser Glu Asn Lys Asp Val Thr Val Ala Val Leu Glu Ser Gly
    50                  55                  60

Pro Tyr Ala Gly Asp Arg Phe Val Val Tyr Ala Pro Gly Met Tyr Gly
65                  70                  75                  80

Gln Ala Val Gly Thr Asp Leu Ala Pro Leu Ile Pro Thr Thr Pro Gln
                85                  90                  95

Glu Asn Met Gly Asn Arg Ser Leu Thr Ile Ala Thr Gly Arg Leu Leu
            100                 105                 110

Gly Gly Gly Ser Ala Ile Asn Gly Leu Val Trp Thr Arg Gly Gly Leu
        115                 120                 125
```

```
Lys Asp Tyr Asp Ala Trp Glu Glu Leu Gly Asn Pro Gly Trp Asn Gly
            130                 135                 140

Ala Asn Leu Phe Lys Tyr Phe Lys Lys Val Glu Asn Phe Thr Pro Pro
145                 150                 155                 160

Thr Pro Ala Gln Ile Glu Tyr Gly Ala Thr Tyr Gln Lys Ser Ala His
                165                 170                 175

Gly Lys Lys Gly Pro Ile Asp Val Ser Phe Thr Asn Tyr Glu Phe Ser
                180                 185                 190

Gln Ser Ala Ser Trp Asn Ala Ser Leu Glu Thr Leu Asp Phe Thr Ala
            195                 200                 205

Leu Pro Asp Ile Leu Asn Gly Thr Leu Ala Gly Tyr Ser Thr Thr Pro
210                 215                 220

Asn Ile Leu Asp Pro Glu Thr Val Arg Arg Val Asp Ser Tyr Thr Gly
225                 230                 235                 240

Tyr Ile Ala Pro Tyr Thr Ser Arg Asn Asn Leu Asn Val Leu Ala Asn
                245                 250                 255

His Thr Val Ser Arg Ile Gln Phe Ala Pro Lys Asn Gly Ser Glu Pro
                260                 265                 270

Leu Lys Ala Thr Gly Val Glu Trp Tyr Pro Thr Gly Asn Lys Asn Gln
            275                 280                 285

Lys Gln Ile Ile Lys Ala Arg Tyr Glu Val Ile Ile Ser Ser Gly Ala
290                 295                 300

Ile Gly Ser Pro Lys Leu Leu Glu Ile Ser Gly Ile Gly Asn Lys Asp
305                 310                 315                 320

Ile Val Ser Ala Ala Gly Val Glu Ser Leu Ile Asp Leu Pro Gly Val
                325                 330                 335

Gly Ser Asn Met Gln Asp His Val His Ala Ile Thr Val Ser Thr Thr
            340                 345                 350

Asn Ile Thr Gly Tyr Thr Thr Asn Ser Val Phe Val Asn Glu Thr Leu
            355                 360                 365

Ala Gln Glu Gln Arg Glu Glu Tyr Glu Ala Asn Lys Thr Gly Ile Trp
370                 375                 380

Ala Thr Cys Pro Asn Asn Leu Gly Tyr Pro Thr Pro Glu Gln Leu Phe
385                 390                 395                 400

Asn Gly Thr Glu Phe Val Ser Gly Lys Glu Phe Ala Asp Lys Ile Arg
                405                 410                 415

Asn Ser Thr Asp Glu Trp Ala Asn Tyr Tyr Ala Ser Thr Asn Ala Ser
            420                 425                 430

Asn Val Glu Leu Leu Lys Lys Gln Tyr Ala Ile Val Ala Ser Arg Tyr
            435                 440                 445

Glu Glu Asn Tyr Leu Ser Pro Ile Glu Ile Asn Phe Thr Pro Gly Tyr
450                 455                 460

Glu Gly Ser Gly Asn Val Asp Leu Gln Asn Asn Lys Tyr Gln Thr Val
465                 470                 475                 480

Asn His Val Leu Ile Ala Pro Leu Ser Arg Gly Tyr Thr His Ile Asn
                485                 490                 495

Ser Ser Asp Val Glu Asp His Ser Val Ile Asn Pro Gln Tyr Tyr Ser
            500                 505                 510

His Pro Met Asp Ile Asp Val His Ile Ala Ser Thr Lys Leu Ala Arg
            515                 520                 525

Glu Ile Ile Thr Ala Ser Pro Gly Leu Gly Asp Ile Asn Ser Gly Glu
530                 535                 540
```

```
Ile Glu Pro Gly Met Asn Ile Thr Ser Asp Asp Val Arg Lys Trp
545                 550                 555                 560

Leu Ser Asn Asn Val Arg Ser Asp Trp His Pro Val Gly Thr Cys Ala
            565                 570                 575

Met Leu Pro Lys Glu Leu Gly Gly Val Val Ser Pro Ala Leu Met Val
        580                 585                 590

Tyr Gly Thr Ser Asn Leu Arg Val Val Asp Ala Ser Ile Met Pro Leu
            595                 600                 605

Glu Val Ser Ser His Leu Met Gln Pro Thr Tyr Gly Ile Ala Glu Lys
        610                 615                 620

Ala Ala Asp Ile Ile Lys Asn Phe Tyr Lys Thr Gln His Lys Asn Gln
625                 630                 635                 640

Asn

<210> SEQ ID NO 4
<211> LENGTH: 1926
<212> TYPE: DNA
<213> ORGANISM: Mucor prainii

<400> SEQUENCE: 4
atgaagatca cagctgccat tatcactgtt gccacagcat ttgcttcttt tgcttctgct      60
caacaagaca caaattcttc ctcaactgat acttatgatt atgttatcgt tggcggcggt     120
gtagctggtt tggctttggc tagtcgtatc tctgaaaaca aggatgtcac tgttgctgtt     180
ctcgagtccg gtccttatgc cggtgataga tttgttgttt atgctcctgg catgtatggc     240
caagctgttg gcactgatct cgctcctctc attcctacta ctcctcaaga aaatatgggc     300
aacagaagtc tcacaatcgc tactggtaga ttgctcggtg gtggcagtgc tattaatggt     360
ctcgtttgga cccgtggtgg cttgaaggat tacgatgctt gggaggagct cggtaaccct     420
ggatggaacg gtgccaactt gttcaagtac tttaagaagg tcgaaaactt cactcctcct     480
actcctgccc aaattgaata cggcgctact tatcagaaaa gtgctcatgg caagaaggga     540
cctattgatg tctctttcac gaactacgag ttctctcaat ctgctagctg aacgcctca      600 ctcgaaaccc ttgatttcac tgcacttcct gatatcttga acggtacttt ggccggttac     660
tctaccactc ccaacatttt ggaccctgag actgttcgac gtgttgattc ctatactggt     720
tacattgctc cttacactag ccgtaacaac ctcaatgttt tggccaacca taccgtctcc     780
cgcattcaat tgctcccaa gaatggtagc gaacctctca aggctaccgg tgttgaatgg     840
tatcccactg gcaacaagaa tcaaaagcaa attatcaagg cccgttatga agttatcatc     900
tcatctggtg ccattggtag tcctaagctt ttggaaatct ctggtatcgg taataaggat     960
atcgtctctg ctgctggtgt cgagtccttg attgacttgc ctggcgttgg ttccaacatg    1020
caagatcacg ttcatgctat cactgtctct actaccaata ttactggcta tactaccaac    1080
agcgtctttg tcaatgaaac ccttgcccaa gaacaaagag aagaatatga agccaacaag    1140
actggtatct gggctacttg tcccaacaac ctcggttatc ctacgcccga caactcttc     1200 aatggcaccg aattcgtttc tggaaaggag tttgctgaca agattcgtaa ctctactgat    1260
gaatgggcca actattatgc ttccaccaac gcctccaatg tcgagttatt aaagaagcaa    1320
tatgctattg tcgcctctcg ttacgaagag aactacttgt ctcctattga aatcaacttc    1380
actcctggtt atgagggtag cggtaatgtc gatttgcaaa acaacaagta ccaaactgtc    1440
aaccatgtct tgattgctcc tttaagtcgt ggttatactc acattaactc ttctgatgtg    1500
gaggatcatt ctgtcattaa tccccaatac tactctcatc ctatggatat tgatgtccat    1560
```

```
atcgcttcca ctaaacttgc tcgcgaaatc atcactgcct ctcccggtct tggtgacatt    1620
aacagtggcg aaatcgaacc cggtatgaat attacttctg acgacgacgt tagaaaatgg    1680
ttgagtaata atgtccgttc tgactggcat cctgttggta cttgtgctat gcttcccaag    1740
gaattaggtg gtgttgtcag ccccgctctc atggtttacg gcacttccaa cttgcgtgtt    1800
gttgatgctt cgattatgcc cctcgaagtc tcttctcatt tgatgcaacc cacctacggt    1860
attgctgaga aggctgctga cattattaag aatttctaca agactcaaca caagaaccaa    1920
aattag                                                               1926
```

<210> SEQ ID NO 5
<211> LENGTH: 30
<212> TYPE: DNA
<213> ORGANISM: Artificial
<220> FEATURE:
<223> OTHER INFORMATION: primer

<400> SEQUENCE: 5
tatcagaaaa gttgtcatgg caagaaggga                                     30

<210> SEQ ID NO 6
<211> LENGTH: 30
<212> TYPE: DNA
<213> ORGANISM: Artificial
<220> FEATURE:
<223> OTHER INFORMATION: primer

<400> SEQUENCE: 6
agagacatca ataggtccct tcttgccatg                                     30

<210> SEQ ID NO 7
<211> LENGTH: 30
<212> TYPE: DNA
<213> ORGANISM: Artificial
<220> FEATURE:
<223> OTHER INFORMATION: primer

<400> SEQUENCE: 7
cctgatatct tgtgcggtac tttggccggt                                     30

<210> SEQ ID NO 8
<211> LENGTH: 30
<212> TYPE: DNA
<213> ORGANISM: Artificial
<220> FEATURE:
<223> OTHER INFORMATION: primer

<400> SEQUENCE: 8
gggagtggta gagtaaccgg ccaaagtacc                                     30

<210> SEQ ID NO 9
<211> LENGTH: 30
<212> TYPE: DNA
<213> ORGANISM: Artificial
<220> FEATURE:
<223> OTHER INFORMATION: primer

<400> SEQUENCE: 9
cctggttatg aggacagcgg taatgtcgat                                     30

<210> SEQ ID NO 10
<211> LENGTH: 30
<212> TYPE: DNA

<213> ORGANISM: Artificial
<220> FEATURE:
<223> OTHER INFORMATION: primer

<400> SEQUENCE: 10
cttgttgttt tgcaaatcga cattaccgct                30

<210> SEQ ID NO 11
<211> LENGTH: 641
<212> TYPE: PRT
<213> ORGANISM: Mucor prainii

<400> SEQUENCE: 11

```
Met Lys Ile Thr Ala Ala Ile Ile Thr Val Ala Thr Ala Phe Ala Ser
1               5                   10                  15

Phe Ala Ser Ala Gln Gln Asp Thr Asn Ser Ser Thr Asp Thr Tyr
            20                  25                  30

Asp Tyr Val Ile Val Gly Gly Gly Val Ala Gly Leu Ala Leu Ala Ser
                35                  40                  45

Arg Ile Ser Glu Asn Lys Asp Val Thr Val Ala Val Leu Glu Ser Gly
    50                  55                  60

Pro Tyr Ala Gly Asp Arg Phe Val Val Tyr Ala Pro Gly Met Tyr Gly
65                  70                  75                  80

Gln Ala Val Gly Thr Asp Leu Ala Pro Leu Ile Pro Thr Thr Pro Gln
                85                  90                  95

Glu Asn Met Gly Asn Arg Ser Leu Thr Ile Ala Thr Gly Arg Leu Leu
            100                 105                 110

Gly Gly Gly Ser Ala Ile Asn Gly Leu Val Trp Thr Arg Gly Gly Leu
        115                 120                 125

Lys Asp Tyr Asp Ala Trp Glu Glu Leu Gly Asn Pro Gly Trp Asn Gly
130                 135                 140

Ala Asn Leu Phe Lys Tyr Phe Lys Lys Val Glu Asn Phe Thr Pro Pro
145                 150                 155                 160

Thr Pro Ala Gln Ile Glu Tyr Gly Ala Thr Tyr Gln Lys Ser Cys His
                165                 170                 175

Gly Lys Lys Gly Pro Ile Asp Val Ser Phe Thr Asn Tyr Glu Phe Ser
            180                 185                 190

Gln Ser Ala Ser Trp Asn Ala Ser Leu Glu Thr Leu Asp Phe Thr Ala
        195                 200                 205

Leu Pro Asp Ile Leu Cys Gly Thr Leu Ala Gly Tyr Ser Thr Thr Pro
    210                 215                 220

Asn Ile Leu Asp Pro Glu Thr Val Arg Arg Val Asp Ser Tyr Thr Gly
225                 230                 235                 240

Tyr Ile Ala Pro Tyr Thr Ser Arg Asn Asn Leu Asn Val Leu Ala Asn
                245                 250                 255

His Thr Val Ser Arg Ile Gln Phe Ala Pro Lys Asn Gly Ser Glu Pro
            260                 265                 270

Leu Lys Ala Thr Gly Val Glu Trp Tyr Pro Thr Gly Asn Lys Asn Gln
        275                 280                 285

Lys Gln Ile Ile Lys Ala Arg Tyr Glu Val Ile Ile Ser Ser Gly Ala
    290                 295                 300

Ile Gly Ser Pro Lys Leu Leu Glu Ile Ser Gly Ile Gly Asn Lys Asp
305                 310                 315                 320

Ile Val Ser Ala Ala Gly Val Glu Ser Leu Ile Asp Leu Pro Gly Val
                325                 330                 335
```

```
Gly Ser Asn Met Gln Asp His Val His Ala Ile Thr Val Ser Thr Thr
                340                 345                 350

Asn Ile Thr Gly Tyr Thr Thr Asn Ser Val Phe Val Asn Glu Thr Leu
            355                 360                 365

Ala Gln Glu Gln Arg Glu Glu Tyr Glu Ala Asn Lys Thr Gly Ile Trp
370                 375                 380

Ala Thr Cys Pro Asn Asn Leu Gly Tyr Pro Thr Pro Glu Gln Leu Phe
385                 390                 395                 400

Asn Gly Thr Glu Phe Val Ser Gly Lys Glu Phe Ala Asp Lys Ile Arg
                405                 410                 415

Asn Ser Thr Asp Glu Trp Ala Asn Tyr Tyr Ala Ser Thr Asn Ala Ser
            420                 425                 430

Asn Val Glu Leu Leu Lys Lys Gln Tyr Ala Ile Val Ala Ser Arg Tyr
        435                 440                 445

Glu Glu Asn Tyr Leu Ser Pro Ile Glu Ile Asn Phe Thr Pro Gly Tyr
    450                 455                 460

Glu Asp Ser Gly Asn Val Asp Leu Gln Asn Asn Lys Tyr Gln Thr Val
465                 470                 475                 480

Asn His Val Leu Ile Ala Pro Leu Ser Arg Gly Tyr Thr His Ile Asn
                485                 490                 495

Ser Ser Asp Val Glu Asp His Ser Val Ile Asn Pro Gln Tyr Tyr Ser
            500                 505                 510

His Pro Met Asp Ile Asp Val His Ile Ala Ser Thr Lys Leu Ala Arg
        515                 520                 525

Glu Ile Ile Thr Ala Ser Pro Gly Leu Gly Asp Ile Asn Ser Gly Glu
    530                 535                 540

Ile Glu Pro Gly Met Asn Ile Thr Ser Asp Asp Val Arg Lys Trp
545                 550                 555                 560

Leu Ser Asn Asn Val Arg Ser Asp Trp His Pro Val Gly Thr Cys Ala
                565                 570                 575

Met Leu Pro Lys Glu Leu Gly Gly Val Val Ser Pro Ala Leu Met Val
            580                 585                 590

Tyr Gly Thr Ser Asn Leu Arg Val Val Asp Ala Ser Ile Met Pro Leu
        595                 600                 605

Glu Val Ser Ser His Leu Met Gln Pro Thr Tyr Gly Ile Ala Glu Lys
    610                 615                 620

Ala Ala Asp Ile Ile Lys Asn Phe Tyr Lys Thr Gln His Lys Asn Gln
625                 630                 635                 640

Asn

<210> SEQ ID NO 12
<211> LENGTH: 1926
<212> TYPE: DNA
<213> ORGANISM: Mucor prainii

<400> SEQUENCE: 12
atgaagatca cagctgccat tatcactgtt gccacagcat ttgcttcttt tgcttctgct     60
caacaagaca caaattcttc ctcaactgat acttatgatt atgttatcgt tggcggcggt    120
gtagctggtt tggctttggc tagtcgtatc tctgaaaaca aggatgtcac tgttgctgtt    180
ctcgagtccg gtccttatgc cggtgataga tttgttgttt atgctcctgg catgtatggc    240
caagctgttg gcactgatct cgctcctctc attcctacta ctcctcaaga aaatatgggc    300
aacagaagtc tcacaatcgc tactggtaga ttgctcggtg gtggcagtgc tattaatggt    360
```

```
ctcgtttgga cccgtggtgg cttgaaggat tacgatgctt gggaggagct cggtaaccct    420
ggatggaacg gtgccaactt gttcaagtac tttaagaagg tcgaaaactt cactcctcct    480
actcctgccc aaattgaata cggcgctact tatcagaaaa gttgtcatgg caagaaggga    540
cctattgatg tctctttcac gaactacgag ttctctcaat ctgctagctg aacgcctca    600
ctcgaaaccc ttgatttcac tgcacttcct gatatcttgt gcggtacttt ggccggttac    660
tctaccactc ccaacatttt ggaccctgag actgttcgac gtgttgattc ctatactggt    720
tacattgctc cttacactag ccgtaacaac ctcaatgttt tggccaacca taccgtctcc    780
cgcattcaat ttgctcccaa gaatggtagc gaacctctca aggctaccgg tgttgaatgg    840
tatcccactg caacaagaa tcaaaagcaa attatcaagg cccgttatga agttatcatc    900
tcatctggtg ccattggtag tcctaagctt ttggaaatct ctggtatcgg taataaggat    960
atcgtctctg ctgctggtgt cgagtccttg attgacttgc ctggcgttgg ttccaacatg   1020
caagatcacg ttcatgctat cactgtctct actaccaata ttactggcta tactaccaac   1080
agcgtctttg tcaatgaaac ccttgcccaa gaacaaagag aagaatatga agccaacaag   1140
actggtatct gggctacttg tcccaacaac ctcggttatc ctacgcccga caactcttc    1200
aatggcaccg aattcgtttc tggaaaggag tttgctgaca agattcgtaa ctctactgat   1260
gaatgggcca actattatgc ttccaccaac gcctccaatg tcgagttatt aaagaagcaa   1320
tatgctattg tcgcctctcg ttacgaagag aactacttgt ctcctattga aatcaacttc   1380
actcctggtt atgaggacag cggtaatgtc gatttgcaaa acaacaagta ccaaactgtc   1440
aaccatgtct tgattgctcc tttaagtcgt ggttatactc acattaactc ttctgatgtg   1500
gaggatcatt ctgtcattaa tccccaatac tactctcatc ctatggatat tgatgtccat   1560
atcgcttcca ctaaacttgc tcgcgaaatc atcactgcct ctcccggtct tggtgacatt   1620
aacagtggcg aaatcgaacc cggtatgaat attacttctg acgacgacgt tagaaaatgg   1680
ttgagtaata atgtccgttc tgactggcat cctgttggta cttgtgctat gcttcccaag   1740
gaattaggtg gtgttgtcag ccccgctctc atggtttacg gcacttccaa cttgcgtgtt   1800
gttgatgctt cgattatgcc cctcgaagtc tcttctcatt tgatgcaacc cacctacggt   1860
attgctgaga aggctgctga cattattaag aatttctaca agactcaaca caagaaccaa   1920
aattag                                                              1926
```

<210> SEQ ID NO 13  
<211> LENGTH: 635  
<212> TYPE: PRT  
<213> ORGANISM: Mucor hiemalis

<400> SEQUENCE: 13

```
Met Lys Ile Ser Val Ala Ile Val Thr Ile Ala Ala Ala Phe Ala Ser
1               5                   10                  15

Phe Ala Asn Ala Gln Lys Thr Ala Thr Ser Asn Thr Tyr Asp Tyr Val
            20                  25                  30

Ile Val Gly Gly Gly Val Gly Gly Leu Ala Leu Ala Ser Arg Leu Ser
        35                  40                  45

Glu Asp Lys Ser Val Thr Val Ala Val Leu Glu Ala Gly Pro Asn Ala
    50                  55                  60

Asp Glu Gln Phe Val Val Tyr Ala Pro Gly Met Tyr Gly Gln Ala Val
65                  70                  75                  80

Gly Thr Asp Leu Cys Pro Leu Arg Pro Thr Val Pro Gln Glu Ala Met
                85                  90                  95
```

```
Asn Asn Arg Thr Leu Thr Ile Ala Thr Gly Lys Leu Leu Gly Gly
            100                 105                 110

Ser Ala Ile Asn Gly Leu Val Trp Thr Arg Gly Ala Leu Lys Asp Phe
        115                 120                 125

Asp Ala Trp Glu Glu Leu Gly Asn Pro Gly Trp Asn Gly Arg Thr Met
130                 135                 140

Phe Lys Tyr Phe Lys Lys Val Glu Arg Phe His Pro Pro Thr Lys Ala
145                 150                 155                 160

Gln Val Gln Tyr Gly Ala Thr Tyr Gln Lys Gly Val His Gly Lys Asn
                165                 170                 175

Gly Arg Ile Asp Ile Ser Phe Pro Glu Phe Gln Phe Pro Gln Ser Ala
            180                 185                 190

Asn Trp Asn Ala Ser Leu Ala Thr Leu Asp Phe Thr His Gln Gln Asp
        195                 200                 205

Leu Leu Asn Gly Ser Leu His Gly Tyr Ser Thr Thr Pro Asn Thr Leu
210                 215                 220

Asp Pro Lys Thr Ala Arg Arg Val Asp Ser Tyr Thr Gly Tyr Ile Ala
225                 230                 235                 240

Pro Phe Val Ser Arg Lys Asn Leu Phe Val Leu Ala Asn His Thr Val
                245                 250                 255

Ser Arg Ile Gln Phe Lys Pro Lys Asn Gly Thr Glu Leu Leu Lys Ala
            260                 265                 270

Val Gly Val Glu Trp Tyr Thr Thr Gly Asp Asn Ser Asn Lys Gln Thr
        275                 280                 285

Ile Lys Ala Arg Arg Glu Val Ile Val Ser Ser Gly Ser Ile Gly Ser
290                 295                 300

Pro Lys Leu Leu Glu Ile Ser Gly Ile Gly Asn Lys Asp Ile Val Thr
305                 310                 315                 320

Ala Ala Gly Val Gln Ser Leu Ile Asp Leu Pro Gly Val Gly Ser Asn
                325                 330                 335

Met Gln Asp His Val His Ala Val Thr Val Ser Thr Thr Asn Ile Thr
            340                 345                 350

Gly Phe Thr Thr Asp Ser Val Phe Gln Asn Glu Thr Leu Ala Glu Glu
        355                 360                 365

Gln Arg Gln Gln Tyr Tyr Asn Asn Lys Thr Gly Ile Trp Thr Thr Thr
370                 375                 380

Pro Asn Asn Leu Gly Tyr Pro Ser Pro Ser Gln Leu Phe Asp Gly Thr
385                 390                 395                 400

Ser Phe Glu Ser Gly Gln Ala Phe Ala Asn Arg Ile Arg Asn Ser Thr
                405                 410                 415

Asp Gln Trp Ala Glu Tyr Tyr Ala Ser Thr Asn Ala Thr Asn Ile Glu
            420                 425                 430

Leu Leu Lys Lys Gln Tyr Ala Ile Val Ala Ser Arg Tyr Glu Glu Asn
        435                 440                 445

Tyr Leu Ser Pro Ile Glu Ile Asn Phe Thr Pro Gly Tyr Gly Gly Thr
450                 455                 460

Thr Asp Val Asp Leu Lys Asn Asn Lys Tyr Gln Thr Val Asn His Val
465                 470                 475                 480

Leu Ile Ala Pro Leu Ser Arg Gly Tyr Thr His Ile Asn Ser Ser Asn
                485                 490                 495

Ile Glu Asp Pro Val Val Ile Asn Pro Gln Tyr Tyr Thr His Pro Met
            500                 505                 510
```

```
Asp Val Asp Val His Ile Ala Ser Thr Lys Leu Ala Arg Arg Ile Leu
            515                 520                 525

Gly Ala Glu Pro Gly Leu Ala Ser Ile Asn Ser Gly Glu Ile Gln Pro
        530                 535                 540

Gly Ser Asn Ile Thr Ser Asp Glu Asp Val Lys Gln Trp Leu Ala Asp
545                 550                 555                 560

Asn Val Arg Ser Asp Trp His Pro Val Gly Thr Cys Ala Met Leu Pro
                565                 570                 575

Arg Glu Leu Gly Gly Val Val Asp Pro Asn Leu Leu Val Tyr Gly Thr
            580                 585                 590

Ala Asn Leu Arg Val Val Asp Ala Ser Ile Met Pro Leu Glu Ile Ser
        595                 600                 605

Ser His Leu Met Gln Pro Thr Tyr Gly Val Ala Glu Lys Ala Ala Asp
    610                 615                 620

Ile Ile Lys Met Ser Arg Lys Asn Asn Asn Asn
625                 630                 635

<210> SEQ ID NO 14
<211> LENGTH: 1908
<212> TYPE: DNA
<213> ORGANISM: Mucor hiemalis

<400> SEQUENCE: 14
atgaaaatct cagtagccat tgtcactatc gccgccgcct tcgcttcctt cgccaacgcc      60
caaaagaccg caaccagtaa tacctatgat tatgtaattg ttggtggtgg tgttggtggt     120
ttggcattag cctctagatt gtcagaagat aaatctgtca cagtagctgt tttagaagca     180
ggtcctaatg ccgacgaaca atttgttgtc tatgccccag gcatgtacgg tcaagctgtt     240
ggtaccgatt gtgtccatt aagacctact gtcccacaag aagctatgaa taacagaaca     300
ttgaccatag caaccggtaa attgttaggt ggtggttcag ctatcaatgg tttggtttgg     360
actagaggtg cattaaagga ttttgacgcc tgggaagaat taggtaatcc aggttggaac     420
ggtagaacta tgttcaagta cttcaaaaag gttgaaagat tccatccacc tacaaaggct     480
caagtccaat atggtgcaac ctaccaaaaa ggtgtacacg gtaaaaatgg tagaatcgat     540
atttcttttc ctgaatttca attcccacaa tctgctaatt ggaacgcctc attggctacc     600
ttagatttca ctcatcaaca agacttgtta aatggttcct gcacggtta tagtactaca     660 cctaacacat tagatccaaa aaccgccaga agagttgact cctatacagg ttacattgct     720
cctttcgtta gtagaaagaa tttgttcgtc ttagcaaaac catactgtat cagaatacaa     780
ttcaaaccaa gaatggtac agaattgttg aaggctgtcg gtgtagaatg gtacaccact     840
ggtgacaact caaacaaaca aacaattaag gcaagaagag aagttatcgt ctcttcaggt     900
tccattggta gtcctaaatt gttggaaata tccggtatcg gtaataagga tatcgtaact     960
gctgcaggtg ttcaatcttt gattgatttg ccaggtgtag gttcaaacat gcaagaccat    1020
gttcacgctg taactgtttc cacaaccaac ataacaggtt ttactacaga tagtgttttc    1080
caaaacgaaa cattggcaga agaacaaaga caacaatact acaacaacaa accggtatc    1140 tggaccacta caccaaataa cttgggttat ccatccccta gtcaattatt tgatggtaca    1200
tctttcgaat caggtcaagc atttgcaaac agaattagaa actctaccga ccaatgggct    1260
gaatattacg catcaactaa tgccacaaac atcgaattgt tgaagaaaca atacgcaatc    1320
gttgcctcca gatacgaaga aaactacttg agtcctatcg aaatcaactt cactccaggt    1380
tatggtggta ccactgatgt tgatttgaaa aataacaagt accaaactgt taatcatgtc    1440
```

```
ttgatcgctc ctttatcaag aggttataca cacatcaatt ccagtaacat agaagatcct    1500
gtagttataa atccacaata ctacacccat ccaatggatg tcgacgtaca cattgcttct    1560
actaaattgg caagaagaat attaggtgcc gaacctggtt tggcttccat aaatagtggt    1620
gaaatccaac caggttctaa cattacatca gatgaagacg ttaagcaatg gttagcagat    1680
aatgttagat ctgactggca tcctgtcggt acatgcgcca tgttgccaag agaattaggt    1740
ggtgtcgtag atccaaattt gttggtttac ggtactgcaa acttaagagt tgtcgacgcc    1800
tctataatgc ctttggaaat ctcttcacat ttgatgcaac caacttacgg tgttgctgaa    1860
aaagccgctg atattattaa gatgtctaga aagaataaca ataactaa                 1908
```